(12) United States Patent
Shtern et al.

(10) Patent No.: US 12,042,315 B2
(45) Date of Patent: Jul. 23, 2024

(54) ROTATING NUCLEAR MEDICINE DETECTOR WITH TWO COLLIMATORS

(71) Applicant: GE Precision Healthcare LLC, Wauwatosa, WI (US)

(72) Inventors: Asaf Shtern, Moshav Betset (IL); Michael Luybansky, Haifa (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 191 days.

(21) Appl. No.: 17/861,554

(22) Filed: Jul. 11, 2022

(65) Prior Publication Data
US 2024/0008829 A1 Jan. 11, 2024

(51) Int. Cl.
*A61B 6/42* (2024.01)

(52) U.S. Cl.
CPC ................... *A61B 6/4258* (2013.01)

(58) Field of Classification Search
CPC ........ A61B 6/4258; G01T 7/00; G01T 1/2907
See application file for complete search history.

(56) References Cited

U.S. PATENT DOCUMENTS

| | | | | |
|---|---|---|---|---|
| 3,291,990 A | * | 12/1966 | Lentz | G01T 7/00 250/366 |
| 3,978,336 A | * | 8/1976 | Roux | G01T 1/2978 250/369 |
| 4,529,882 A | * | 7/1985 | Lee | G01T 1/2928 250/363.02 |
| 5,638,817 A | * | 6/1997 | Morgan | G01T 1/1615 250/363.1 |
| 9,554,489 B2 | | 1/2017 | Hefetz et al. | |
| 10,761,224 B2 | | 9/2020 | Bouhnik et al. | |
| 2007/0025513 A1 | | 2/2007 | Ghelmansarai | |
| 2007/0221853 A1 | * | 9/2007 | Joung | G21K 1/04 250/363.09 |

(Continued)

FOREIGN PATENT DOCUMENTS

WO 2020195685 A1 10/2020

OTHER PUBLICATIONS

U.S. Appl. No. 17/519,756, filed Nov. 5, 2021, Jean-Paul Bouhnik et al.

(Continued)

*Primary Examiner* — Kiho Kim
(74) *Attorney, Agent, or Firm* — Fletcher Yoder P.C.

(57) ABSTRACT

A radiation detector head assembly includes a detector column including a detector having a first surface and a second surface opposite the first surface. The detector column includes a first collimator disposed over the first surface of the detector and a second collimator disposed over the second surface of the detector. The detector column includes a first radiation shield disposed over the first collimator, wherein the first radiation shield includes a first recess for receiving the first collimator and a first opening over a third surface of the first collimator, the third surface being opposite the first surface of the detector. The detector column includes a second radiation shield disposed over the second collimator, wherein the second radiation shield includes a second recess for receiving the second collimator and a second opening over a fourth surface of the second collimator, the fourth surface being opposite the second surface.

20 Claims, 23 Drawing Sheets

(56) References Cited

U.S. PATENT DOCUMENTS

| | | |
|---|---|---|
| 2010/0246754 A1 | 9/2010 | Morton |
| 2015/0085970 A1 | 3/2015 | Bouhnik et al. |
| 2016/0077217 A1 | 3/2016 | Shahar |
| 2016/0170038 A1 | 6/2016 | Yu |
| 2018/0236267 A1 | 8/2018 | Kuang et al. |
| 2019/0223816 A1 | 7/2019 | Bouhnik et al. |

OTHER PUBLICATIONS

EP application 23184248.5 filed Jul. 7, 2023—extended Search Report issued Nov. 21, 2023; 11pages.

\* cited by examiner

ROTATING NUCLEAR MEDICINE DETECTOR WITH TWO COLLIMATORS

BACKGROUND

The subject matter disclosed herein relates to medical imaging systems and, more particularly, to radiation detection systems.

In nuclear medicine (NM) imaging, such as single photon emission computed tomography (SPECT), radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having several individual detectors distributed about the gantry. Each detector (e.g., detector head) may pivot or sweep to provide a range over which the detector may acquire information that is larger than a stationary field of view of the detector. Detectors in nuclear medicine need to absorb x- or gamma-ray photons over a wide energy range. Depending on the application (low/medium energy versus high energy), a different collimator may be utilized for collimation. However, changing out the collimator for each detectors typically involves utilizing a mechanical exchange process to manually replace one collimator utilized with one application with another collimator utilized for another application. Utilization of the mechanical exchange process may be a time consuming process that may take several minutes resulting in down time that hampers workflow (e.g., hospital patient flow).

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a radiation detector head assembly is provided. The radiation detector head assembly includes a detector column. The detector column includes a detector having a first surface and a second surface opposite the first surface. The detector column also includes a first collimator disposed over the first surface of the detector configured for use during imaging scans involving radiation in a first energy range. The detector column further includes a second collimator disposed over the second surface of the detector configured for use during imaging scans involving radiation in a second energy range different from the first energy range. The detector column further includes a first radiation shield disposed over the first collimator, wherein the first radiation shield includes a first recess for receiving the first collimator and a first opening over a third surface of the first collimator, the third surface being opposite the first surface of the detector. The detector column still further includes a second radiation shield disposed over the second collimator, wherein the second radiation shield includes a second recess for receiving the second collimator and a second opening over a fourth surface of the second collimator, the fourth surface being opposite the second surface of the detector.

In another embodiment, a detector column for a nuclear medicine multi-head imaging system is provided. The detector column includes a detector having a first surface and a second surface opposite the first surface. The detector column also includes a first collimator disposed over the first surface of the detector configured for use during imaging scans involving radiation in a first energy range. The detector column further includes a second collimator disposed over the second surface of the detector configured for use during imaging scans involving radiation in a second energy range different from the first energy range. The detector column yet further includes radiation shielding encompassing the detector, the first collimator, and the second collimator. The detector column still further includes a module board having digital electronics disposed outside the radiation shielding of the detector column.

In a further embodiment, a radiation detector head assembly is provided. The radiation detector head assembly includes a detector column. The detector column includes a detector having a first surface and a second surface opposite the first surface. The detector column also includes a first collimator disposed over the first surface of the detector configured for use during imaging scans involving radiation in a first energy range. The detector column further includes a second collimator disposed over the second surface of the detector configured for use during imaging scans involving radiation in a second energy range different from the first energy range. The detector column is configured to rotate greater than 360 degrees about its longitudinal axis.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
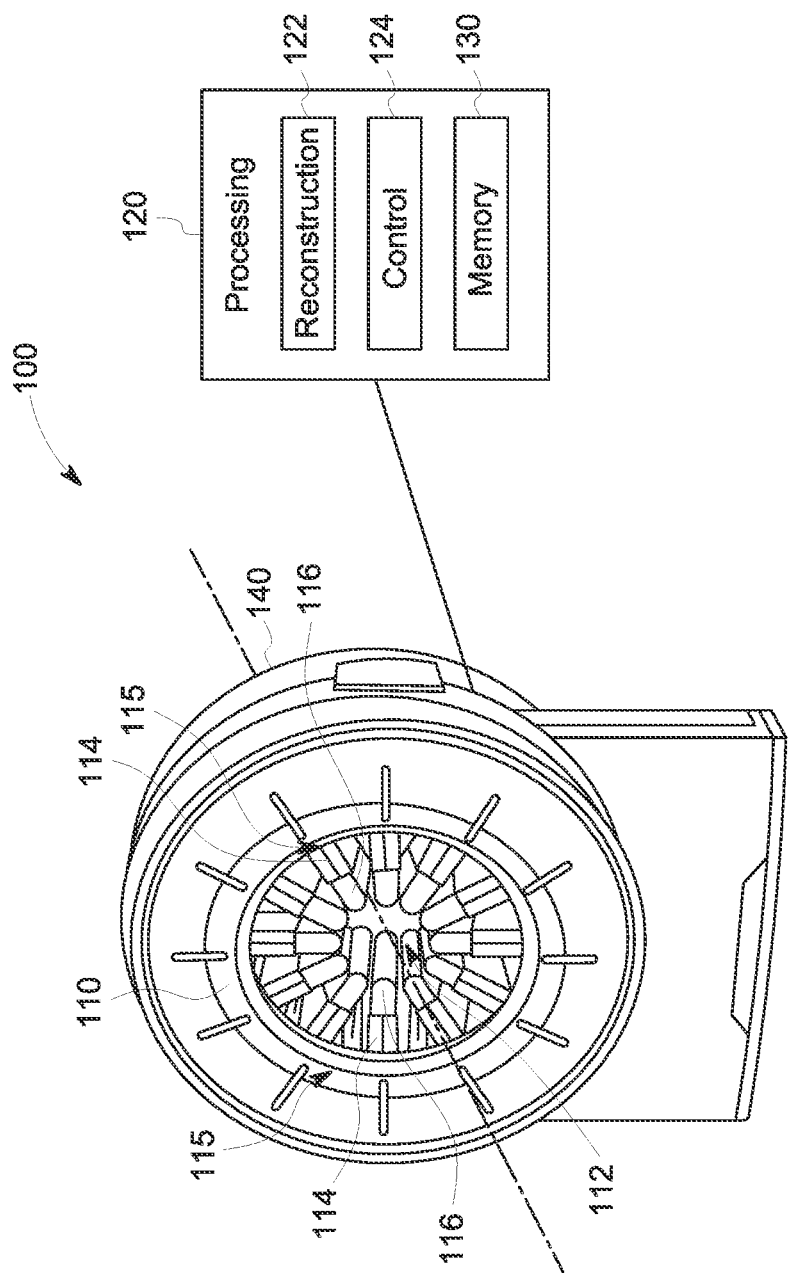
FIG. 1 is a schematic view of a nuclear imaging system, in accordance with aspects of the disclosed techniques.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides systems and methods for utilizing at least two collimators within a radiation detector head assembly of a nuclear medicine (NM) multi-head imaging system. In particular, each detector head of the NM multi-head imaging system includes a detector column that includes a semiconductor detector having a first surface that includes a cathode and a second surface that includes pixelated anodes, where a respective collimator is disposed over both the first surface and the second surface of the semiconductor detector. The collimator disposed over the cathode is configured for utilization during an imaging scan involving radiation in a first energy range (e.g., low energy range of approximately 40 to 300 keV) and the collimator disposed over the pixelated anodes is configured for utilization during an imaging scan involving radiation in a second energy range (e.g., high energy range of approximately 250 to 400 keV) different from the first energy range. The first and second energy ranges may partially overlap (e.g., at a high end of the first energy range and a low end of the second energy range) but differ in extent. Rotation about a longitudinal axis (e.g., sweeping axis) of the detector head (e.g., via a motor) enables the collimators to be interchanged between scans or during the same scan (e.g., dual isotopes applications) involving different levels of energy (e.g., low energy versus high energy). The disclosed embodiments enable the automatic interchange between the different collimators to occurs within a matter of seconds (e.g., as opposed to minutes). The interchange occurs completely within the radiation detector head assembly (without having to remove one of the collimators or mounting the collimator to be utilized) and without the utilization of a mechanical (and manual) collimator exchange process. The quick automatic exchange between collimators saves time during the day and avoids downtime for the imaging system, thus, enabling an improved workflow (e.g., hospital patient flow). The disclosed embodiments may also reduce the cost of the imaging system.

FIG. 1 provides a schematic view of a NM multi-head imaging system 100 in accordance with various embodiments. Generally, the imaging system 100 is configured to acquire imaging information or data (e.g., photon counts) from an object to be imaged (e.g., a human patient) that has been administered a radiopharmaceutical. The depicted imaging system 100 includes a gantry 110 and a processing unit 120.

The gantry 110 defines a bore 112. The bore 112 is configured to accept an object to be imaged (e.g., a human patient or portion thereof). As seen in FIG. 1, a plurality of detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. In certain embodiments, the detector of the head 116 may include a scintillator with a silicon photomultiplier (SiPM). The detector may be configured for use with, for example, nuclear medicine (NM) imaging systems such as single photon emission computed tomography (SPECT) imaging systems.

In various embodiments, the detector may include an array of pixelated anodes, and may generate different signals depending on the location of where a photon is absorbed in the volume of the detector under a surface if the detector.

The absorption of photons from certain voxels corresponding to particular pixelated anodes results in charges generated that may be counted. The counts may be correlated to particular locations and used to reconstruct an image.

Figure 2:
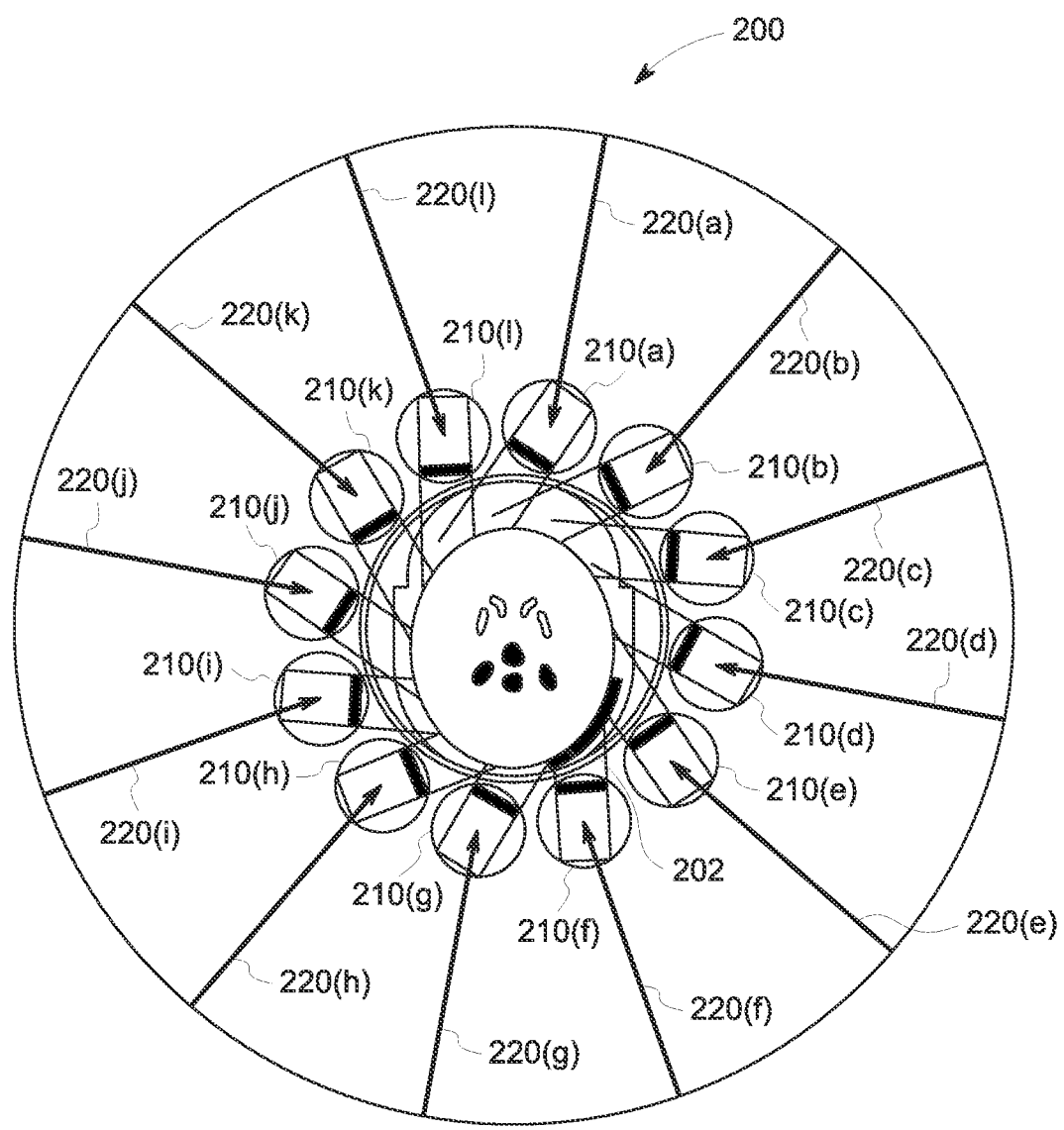
FIG. 2 is a schematic view of a detector arrangement, in accordance with aspects of the disclosed techniques.

In various embodiments, each detector unit 115 may define a corresponding view that is oriented toward the center of the bore 112. Each detector unit 115 in the illustrated embodiment is configured to acquire imaging information over a sweep range corresponding to the view of the given detector unit. FIG. 2 illustrates a detector arrangement 200 in accordance with various embodiments. The detector units of FIG. 1, for example, may be arranged in accordance with aspects of the detector arrangement 200. In some embodiments, the system 100 further includes a CT (computed tomography) detection unit 140. The CT detection unit 140 may be centered about the bore 112. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 112.

As seen in FIG. 2, the detector arrangement 200 includes detector units 210(a), 210(b), 210(c), 210(d), 210(e), 210(f), 210(g), 210(h), 210(i), 210(j), 210(k), 210(l) disposed about and oriented toward (e.g., a detection or acquisition surface of the detector units, and/or the FOV (Field of View), are oriented toward) an object 202 to be imaged in the center of a bore. Each detector unit of the illustrated embodiment defines a corresponding view that may be oriented toward the center of the bore of the detector arrangement 200 (it may be noted that because each detector unit may be configured to sweep or rotate about an axis, the FOV need not be oriented precisely toward the center of the bore, or centered about the center of the bore, at all times). The view for each detector unit 210, for example, may be aligned along a central axis of a corresponding arm (e.g., arm 114) of the detector unit 210. In the illustrated embodiment, the detector unit 210(a) defines a corresponding view 220(a), the detector unit 210(b) defines a corresponding view 220(b), and the detector unit 210(c) defines a corresponding view 220(c), and so on. The detector units 210 are configured to sweep or pivot (thus sweeping the corresponding FOV's) over a sweep range (or portion thereof) bounded on either side of a line defined by the corresponding view during acquisition of imaging information. Thus, each detector unit 210 may collect information over a range larger than a field of view defined by a stationary detector unit. It may be noted that, generally, the sweeping range over which a detector may potentially pivot may be larger than the corresponding view during acquisition. In some cameras, the sweeping range that a detector may pivot may be unlimited (e.g., the detector may pivot a full 360 degrees or less), while in some embodiments the sweeping range of a detector may be constrained, for example over 180 degrees (from a −90 degree position to a +90 degree position relative to a position oriented toward the center of the bore). In certain embodiments, as described in greater detail below, sweeping range of a detector may be greater than 360 degrees. It may be noted that the detector units 210 of FIG. 2 are mounted to a gantry (e.g., gantry 100 in FIG. 1). The gantry may be rotatable to different positions, with the detector units 210 rotating with the gantry.

With continued reference to FIG. 1, the depicted processing unit 120 is configured to acquire imaging information or data (e.g., photon counts) via the detector units 115. In various embodiments the imaging information includes focused imaging information and background imaging information. The focused imaging information corresponds to a focused region, and the background imaging information corresponds to tissues surrounding the focused region. As used herein, both the focused region and surrounding tissue may be used for imaging and/or diagnostic purposes; however, the focused region may be more pertinent or useful for diagnostic purposes, and, accordingly, more imaging information is acquired for the focused region than for the surrounding tissue. An example of a focused region and surrounding tissue is shown in FIG. 3.

Figure 3:
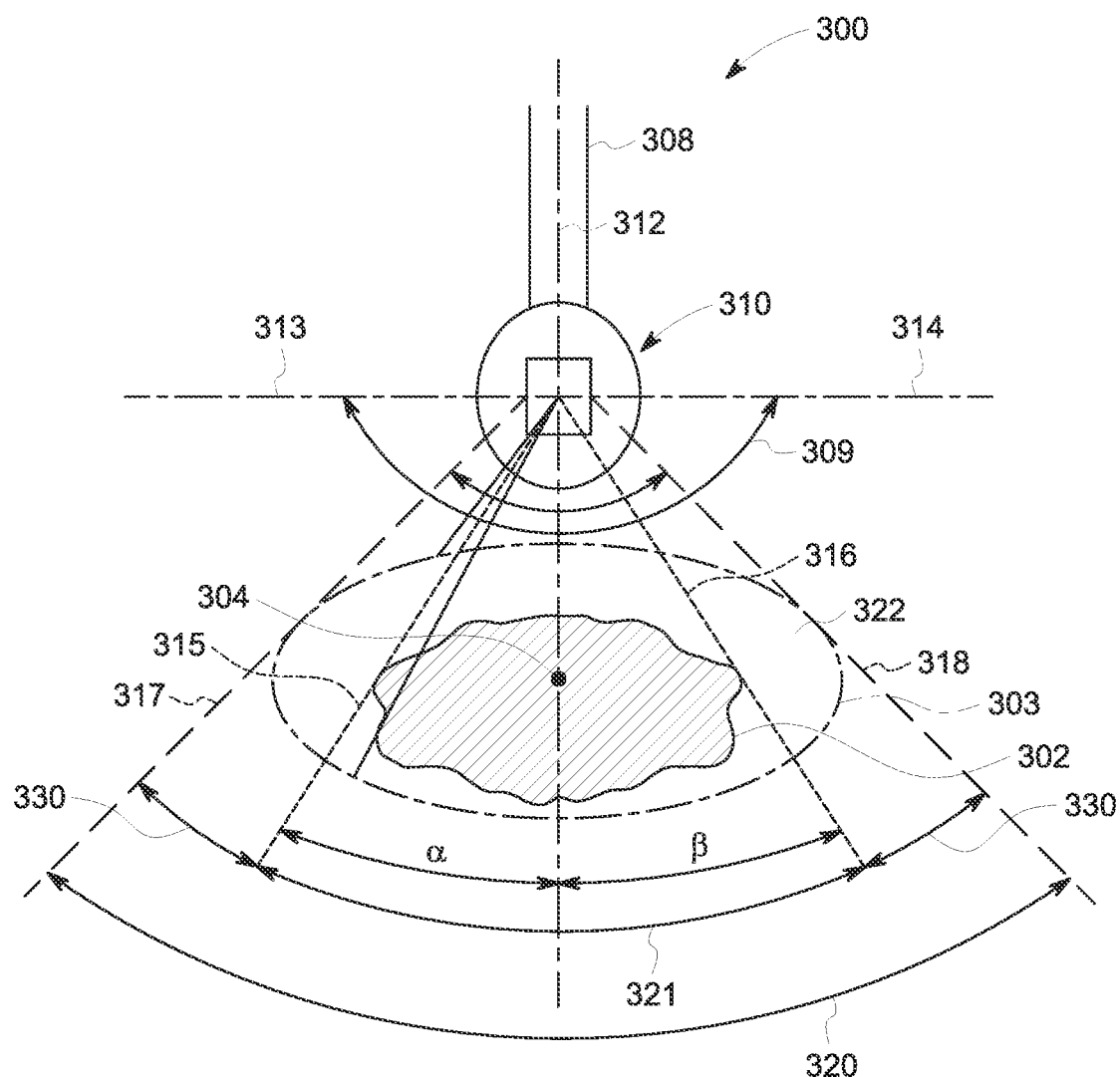
FIG. 3 is a schematic view of sweep and acquisition ranges for a detector unit, in accordance with aspects of the disclosed techniques.

FIG. 3 depicts a focused region and surrounding tissue of an object, or a focused portion and background portion of an image. As seen in FIG. 3, the detector unit 300 includes a detector head 310 disposed at an end of a detector arm 308. In FIG. 3, only one detector unit 300 is depicted for ease and clarity of illustration. It may be noted that the detector unit 300 may be part of an arrangement of plural detector heads, such as depicted in FIGS. 1 and 2, and that the general principles discussed in connection with the detector unit 300 may be applied to one or more additional detector units of a multi-head camera imaging system. In FIG. 3, the detector unit 300 may be used to acquire imaging information (e.g., photon counts) of an object 303 having a focused region 302. In the illustrated embodiment, the focused region 302 is surrounded by surrounding tissue 322. The focused region 302, for example, may be an organ such as the heart or brain (or portion thereof), and may have a substantially larger uptake of an administered radiopharmaceutical than surrounding tissue 322 of the object 303. For example, in some embodiments, the focused region 302 is the striata of the brain, and the surrounding tissue 322 includes other portions of the brain. A ratio of detected activity between the striata and other portions of the brain may be used in analyzing whether or not a patient has Parkinson's disease. A central axis 312 of the detector unit 300 passes through a center 304 of the focused region 302 (which is disposed at the center of a bore in the illustrated embodiment). It may be noted that in various embodiments the central axis or center view of the detector need not necessarily pass through the focus center or through the focused region. The central axis 312, for example, may correspond to a line along the view corresponding to the detector unit 300 when the detector unit 300 is at a midpoint of a range of coverage of the detector unit 300, and/or may be aligned with a central axis of the detector arm 308 to which the detector head 310 is attached.

In the illustrated embodiment, the detector unit 300 is depicted as aligned with the central axis 312, and may be rotated, pivoted or swept over a sweep range 309 between a first limit 313 and a second limit 314. In the illustrated embodiment, the first limit 313 and the second limit 314 define a sweep range 309 (or maximum range of coverage) of 180 degrees. In other embodiments, the sweep range 309 and/or relative positions of the first limit 313 and second limit 314 may vary from the depicted arrangement. It may be noted that the sweep range 309 provides more coverage than is required to collect imaging information of the focused region 302 and the surrounding tissue 322. Thus, if the detector unit 300 is swept over the sweep range 309 during a duration of an imaging acquisition, information that may be not be useful for diagnostic purposes (e.g., information towards the ends of the sweep range 309 that does not include information from either the focused region 302 or the surrounding tissue 322) may be collected. The time used to collect the information that is not useful for diagnostic purposes may be more efficiently spent collecting additional information from the focused region 302 and/or the surrounding tissue 322. Accordingly, in the illustrated embodiment, the detector head 310 may be controlled (e.g., by processing unit 120) to be swept or pivoted over an acquisition range 320 (e.g., a range including the focused region 302 and surrounding tissue 322) instead of over the entire sweep range 309 during acquisition of imaging information.

As seen in FIG. 3, the acquisition range 320 generally corresponds to edges of the surrounding tissue 322, and is bounded by a first boundary 317 and a second boundary 318. A focused range 321 is defined within the acquisition range 320 and corresponds to edges of the focused region 302. The focused range 321 is bounded by a first boundary 315 and a second boundary 316. Generally, more imaging information is acquired over the focused range 321 than over the background portions 330 of the acquisition range 320 which include the surrounding tissue 322 but not the focused region 302. Generally, more time is spent acquiring information over the focused range 321 than over the background portions 330. For example, the detector head 310 may be swept at a higher sweep rate over the background portions 330 when acquiring the background imaging information than over the focused range 321 when acquiring the focused imaging information. The first boundary 315 is located at an angle α in clockwise direction from the central axis 312 (and, in the illustrated embodiment, from the center 304). The second boundary 316 is located at an angle R in a counterclockwise direction from the central axis 312 (and, in the illustrated embodiment, from the center 304).

It may be noted the boundaries may not necessarily correspond to a central axis or portion of a field of view of the detector unit, but may correspond to an edge or other portion of the field of view. Further, the acquisition range 320 may be configured in various embodiments to include more or less surrounding tissue beyond the focused region. Further, the acquisition range 320 may include an amount of background or surrounding tissue for a first phase of an acquisition period and omit background or surrounding tissue for a second phase; or omit the acquisition of surrounding tissue altogether (for one or several detector units comprising the system).

Returning to FIG. 1, in various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may distributed among various units or housings (e.g., one or more aspects of the processing unit 120 may be disposed onboard one or more detector units, and one or more aspects of the processing unit 120 may be disposed in a separate physical unit or housing). The processing unit 120, for example, may switch between different collimators (e.g., configured for different energy applications) depending on the energy application, determine acquisition range boundaries for focused and background regions, control the detector heads to acquire desired amounts of focused and background information, and reconstruct an image as discussed herein. It may be noted that operations performed by the processing unit 120 (e.g., operations corresponding to process flows or methods discussed herein, or aspects thereof) may be sufficiently complex that the operations may not be performed by a human being within a reasonable time period. For example, identifying boundaries of acquisition ranges, providing control signals to detector units, reconstructing images, or the like may rely on or utilize computations that may not be completed by a person within a reasonable time period.

In the illustrated embodiment, the processing unit 120 includes a reconstruction module 122, a control module 124, and a memory 130. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In the illustrated embodiment, the depicted reconstruction module 122 is configured to reconstruct an image. The depicted control module 124 is configured to interchange or switch between different collimators (e.g., configured for different energy applications) depending on the energy application. In addition, the depicted control module 124 is configured to control the detector heads 116 to sweep over corresponding acquisition ranges to acquiring focused imaging information and background imaging information. It may be noted that, in various embodiments, aspects of the control module 124 may be distributed among detector units 115. For example, each detector unit may have a dedicated control module disposed in the head 116 of the detector unit 115.

The memory 130 may include one or more computer readable storage media. The memory 130, for example, may store information describing previously determined boundaries of acquisition ranges, parameters to be utilized during performance of a scan, parameters to be used for reconstruction or the like. Further, the process flows and/or flowcharts discussed herein (or aspects thereof) may represent one or more sets of instructions that are stored in the memory 130 for direction of operations of the imaging system 100.

It may be noted that while the processing unit 120 is depicted schematically in FIG. 1 as separate from the detector units 115, in various embodiments, one or more aspects of the processing unit 120 may be shared with the detector units 115, associated with the detector units 115, and/or disposed onboard the detector units 115. For example, in some embodiments, at least a portion of the processing unit 120 is integrated with at least one of the detector units 115.

Figure 4:
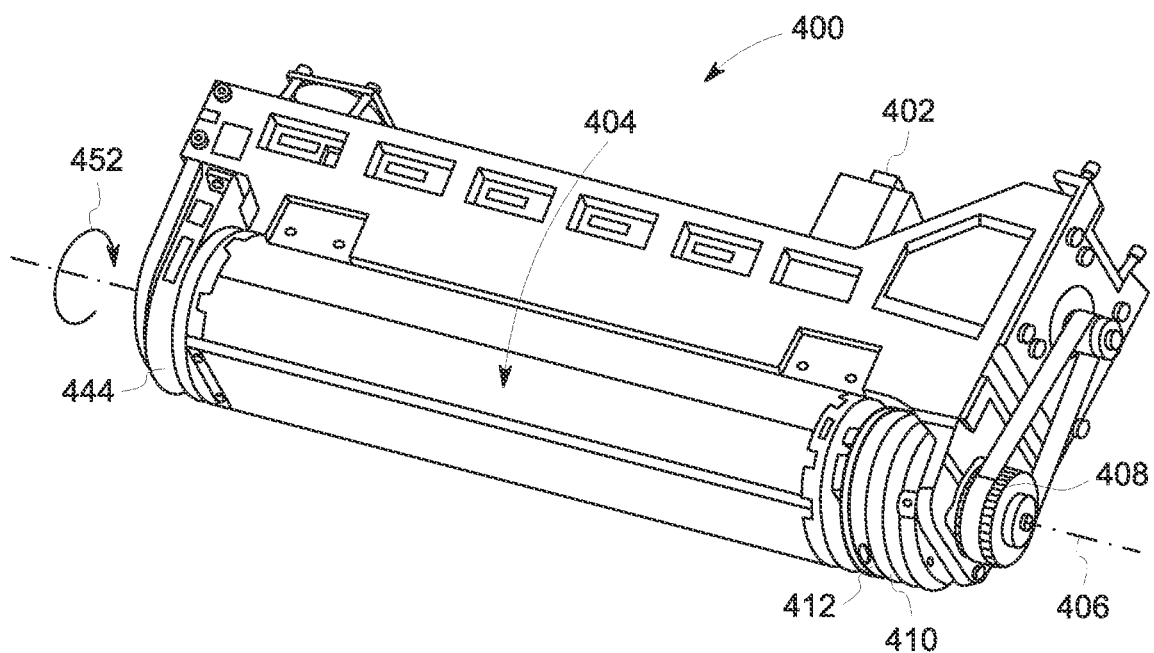
FIG. 4 is perspective view of a detector head, in accordance with aspects of the disclosed techniques.
Figure 5:
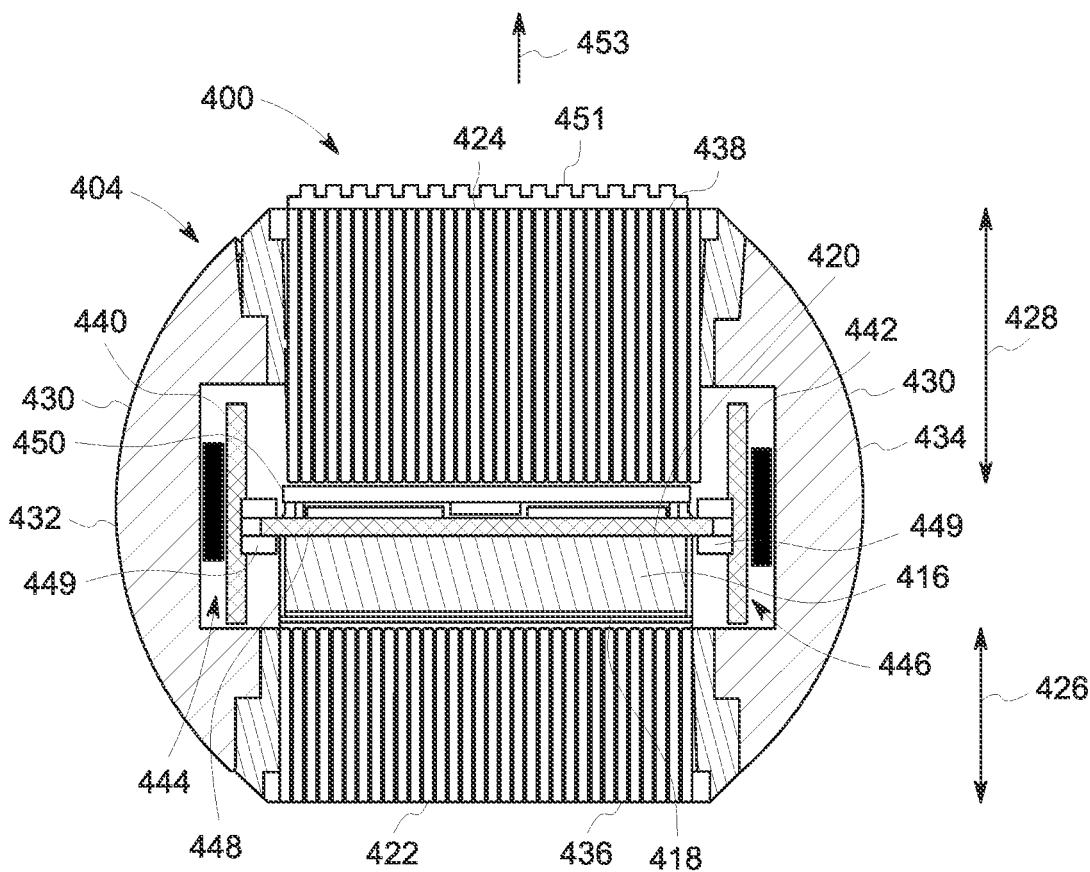
FIG. 5 is a cross-sectional view of the detector head in FIG. 4, in accordance with aspects of the disclosed techniques.

FIG. 4 is a perspective view of an example detector head 400 (e.g., having two collimators for different energy applications) and FIG. 5 is a cross-sectional view (e.g., axial cross section) of the detector head 400. As seen in FIG. 5, the detector head 400 includes a stepper motor 402 that may be utilized to pivot a detector column 404 about its longitudinal axis 406 (e.g., sweeping axis). It may be noted that motors other than stepper motors may be used in various embodiments. The detector head 400 also includes a gear 408 coupling the stepper motor to the detector column 404, as well as a slip ring 410 (configured to allow for transfer of signals between the rotating detector column 404 and non-rotating components) and a multiplex board 412. In the illustrated embodiment, the detector head 400 also includes an air channel 414 configured to provide cooling to components of the detector head 400.

As depicted in FIG. 5, the detector column 404 includes a detector 416 (e.g., semiconductor detector such as CZT detector). The detector 416 includes a first surface 418 having a cathode disposed on it and a second surface 420 having pixelated anodes disposed on it. The detector column 404 includes collimators 422, 424 disposed over both the first surface 418 and the second surface 420 of the semiconductor device, respectively. The collimator 422 disposed over the cathode is configured for utilization during an imaging scan involving radiation in a first energy range (e.g., low energy range of approximately 40 to 300 keV). The collimator 424 disposed over the pixelated anodes is configured for utilization during an imaging scan involving radiation in a second energy range (e.g., high energy range of approximately 250 to 400 keV) different from the first energy range. The terms "high" and "low" as utilized herein are relative, with high energy meaning an energy higher than another energy and low energy meaning an energy lower than another energy. As noted above, the first and second energy ranges may partially overlap (e.g., at a high end of the first energy range and a low end of the second energy range) but differ in extent. As noted above, the collimators 422, 424 may be utilized during the same scan involving dual isotopes (e.g., high and low energy isotopes).

The collimators 422, 424 each have a respective height 426, 428 (e.g., height for the septa). In certain embodiments, the height 428 of the collimator 424 is greater than the height 426 of the collimator 422. In certain embodiments, the ratio of the height 428 to the height 426 may range from 2:1 to 5:4. For example, the ratio of the height 428 to the height 426 may be 2:1, 3:2, 4:3, 5:4, or another ratio. In certain embodiments, the heights 426, 428, of the collimators 422, 424 may be the same. Due to limited space within the detector head 400, the heights 426, 428 of the collimators are limited. In order to avoid degraded spatial resolution due to a limited height collimator and to improve image quality (e.g., due to increased sensitivity, resolution, and/or contrast), sub-pixelization (e.g., either real or virtual sub-pixelization) may be utilized as described in U.S. Pat. No. 10,761,224, entitled "Systems and Methods for Improved Detector Assembly Sizing," issued on Sep. 1, 2020, and incorporated by reference in its entirety.

The detector column 404 includes a radiation shield 430 (e.g., lead shield). In certain embodiments, the radiation shield is an aluminum extrusion having lead. The radiation shield 430 includes a first radiation shield portion 432 and a second radiation shield portion 434 that flank the collimators 422, 424, the detector 416, and associated electronics. In particular, the radiation shield portions 432, 434 extend from adjacent end 436 of the collimator 422 to adjacent end 438 of the collimator 424 in a direction perpendicular to the longitudinal axis 406 (see FIG. 5). The radiation shield portions 432, 424 also extend in a direction along the longitudinal axis 406. In certain embodiments, the collimator 424 enables the detector column 404 to be utilized in imaging applications where a radioactive tracer such as 1131 is utilized. For example with 1131, the collimator provides adequate collimation for the 364 keV gamma ray and good shielding to reduce eventual contamination from 630 keV into the 364 keV peak (e.g., via limited photopeak charge collection efficiency or patient high energy scattered events). During high energy applications, the thickness of the detector 416 provides some radiation shielding in conjunction with the shielding form the radiation shield 430. In addition, the peripheral CZT pixels act as a shield and absorb some of the gamma rays.

Printed circuit boards 440, 442 for electronics (e.g., power boards) are located in respective cavities 444, 446 formed between the radiation shield 430, the collimators 422, 424, and the semiconductor detector 416. The printed circuit boards 440, 442 flank a portion of the collimator 424 and the semiconductor detector 416. The positioning of the printed circuit boards 440, 442 reduces interference due to non-detecting material. In particular, no interfering material is located on the backside (e.g., anode side) to enable gamma ray collection from both the back and front sides of the detector 416. The printed circuit boards 440, 442, may include dedicated routing blocks and field programmable gate arrays. A printed circuit board 448 including an analog front-end including data channels and ASIC is disposed between the collimator 424 and the semiconductor detector 416. A heat sink 450 is disposed between the collimator 424 and the printed circuit board 448. In certain embodiments, the analog-front end associated data channels and ASIC may be located in the same location as the printed circuit boards 440, 442 and coupled via flex circuitry. In such an embodiment, no heat sink would be disposed between the collimator 424 and the detector 416. In addition, in certain embodiments, an additional heat sink 451 may be disposed over the collimator 424 (e.g., on the end 438). The heat sinks 450, 451 may be made from aluminum, brass, or graphene to minimize attenuation. The heat dissipation flow occurs from the detector 416 (e.g., detector module) to the heat sink 450 to the collimator 424 and then to additional heat sink 451.

The detector column 404 also includes connectors 449 (e.g., right angle connectors) to enable removal of the detector 416 (e.g., detector module). In particular, the connectors 449 enable removal of the detector 416 in direction 453.

Figure 6:
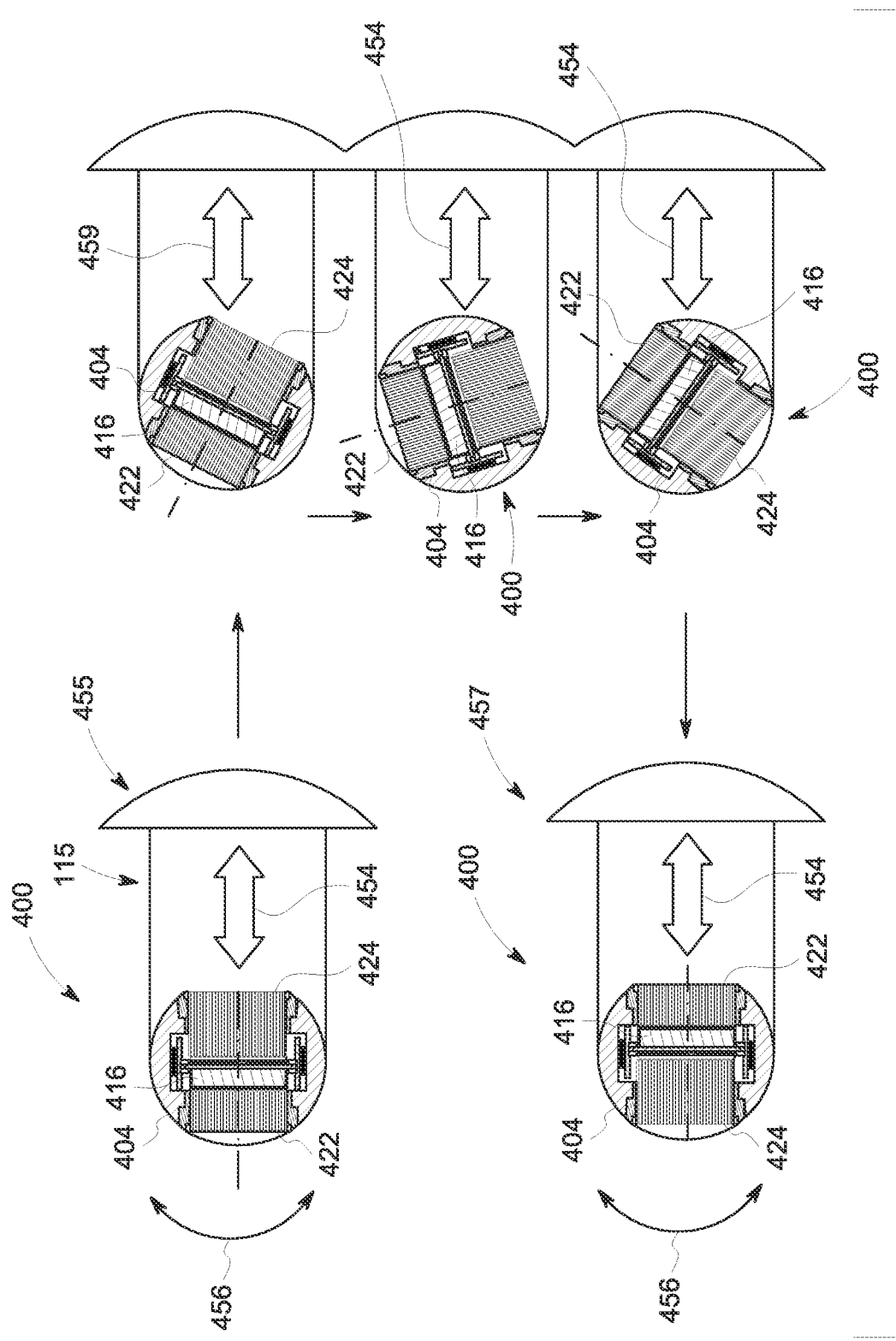
FIG. 6 is a schematic view illustrating switching between usage of different collimators within a detector head assembly, in accordance with aspects of the disclosed techniques.

Returning to FIG. 4, the detector head 400 may be rotated about its longitudinal axis 406 as indicated by arrow 452 to position one of the collimators 422, 424 for use during an imaging scan (i.e., so that the collimator 422, 424 to be used faces the object to be imaged). FIG. 6 is a schematic view illustrating switching between usage of different collimators within a detector head assembly. FIG. 6 depicts a single detector unit 115 of an NM multi-head imaging system. The description of the single detector unit 115 applies to the rest of the detector units 115 of the NM multi-head imaging system. The single detector unit 115 is as described above and includes the detector head 400 as described in FIGS. 4 and 5 having the detector column 404. The detector column 404 includes the detector 416 disposed between the two collimators 422, 424 as described above. The detector unit 115 may move radially in and out as indicated by arrow 454. In addition, the detector column 404 has a sweep motion as indicated by arrow 456. In a first position 455 (e.g., for utilization during a low energy application), the collimator 422 is facing the object to be imaged. In a second position 457 (e.g., for utilization during a high energy application or a dual isotopes application), the collimator 424 is facing the object to be imaged. Utilizing the sweep axis degree of freedom, the detector column 404 may be rotated about its longitudinal axis (e.g., longitudinal axis 406 in FIG. 4) approximately 180 degrees (±180 degrees) to change from the first position to the second position or vice versa as depicted in FIG. 6. Once the detector column 404 is in the desired position (e.g., first or second position), the detector column 404 may be rotated during an image scan a further approximately 105 degrees (±105 degrees). In total, the detector column 404 may rotated up to approximately 285 degrees (±285 degrees). As noted above, the rotation of the detector column 404 occurs via a motor coupled to the detector column 404. In certain embodiments, as described in greater detail below, the detector column 404 may be configured to rotate greater than 360 degrees. The interchanging or switching of the collimators 422, 424 occurs semi-automatically or automatically (e.g., in response to an input or control signal) without removing the collimator 422, 424 from the detector unit 415 and the detector head 400. In certain embodiments, the interchange or switching may be carried out manually.

Figure 7:
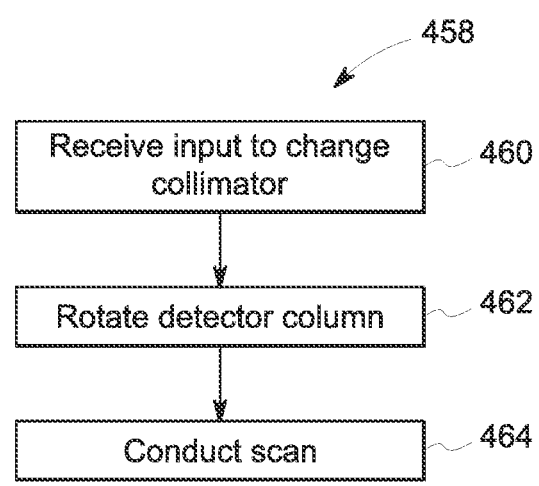
FIG. 7 is a flow chart of a method for switching between collimators in a detector head assembly, in accordance with aspects of the disclosed techniques.

FIG. 7 is a flow chart of an embodiment of a method 458 for switching between collimators in a detector head assembly of a NM multi-head imaging system. The detector head collimator includes two different collimators configured for different energy applications as described above. One or more steps of the method 458 may be performed by a component of the NM multi-head imaging system (e.g., processing unit 120 in FIG. 1). The method 458 includes receiving a receiving an input (e.g., control signal) to change the collimator in the detector head (block 460). The input may be received via an input device of the NM multi-head imaging system. The input may be received in response to selection of a particular imaging scan, a particular radioactive tracer, and a combination thereof. The method 458 also includes rotating (e.g., automatically) the detector column to change the current position of the detector column (e.g., the first position or the second position as described in FIG. 6) to another position (e.g., the second position if initially in the first position or the first position if initially in the second position) if the received input necessitates changing the position of the detector head (block 462). The method 458 further includes conducting the scan with the detector column in the desired position (block 464). In certain embodiments, switching between the two different collimators may occur during the same scan (e.g., applications involving dual isotopes (e.g., high and low energy isotopes)).

Figure 8:
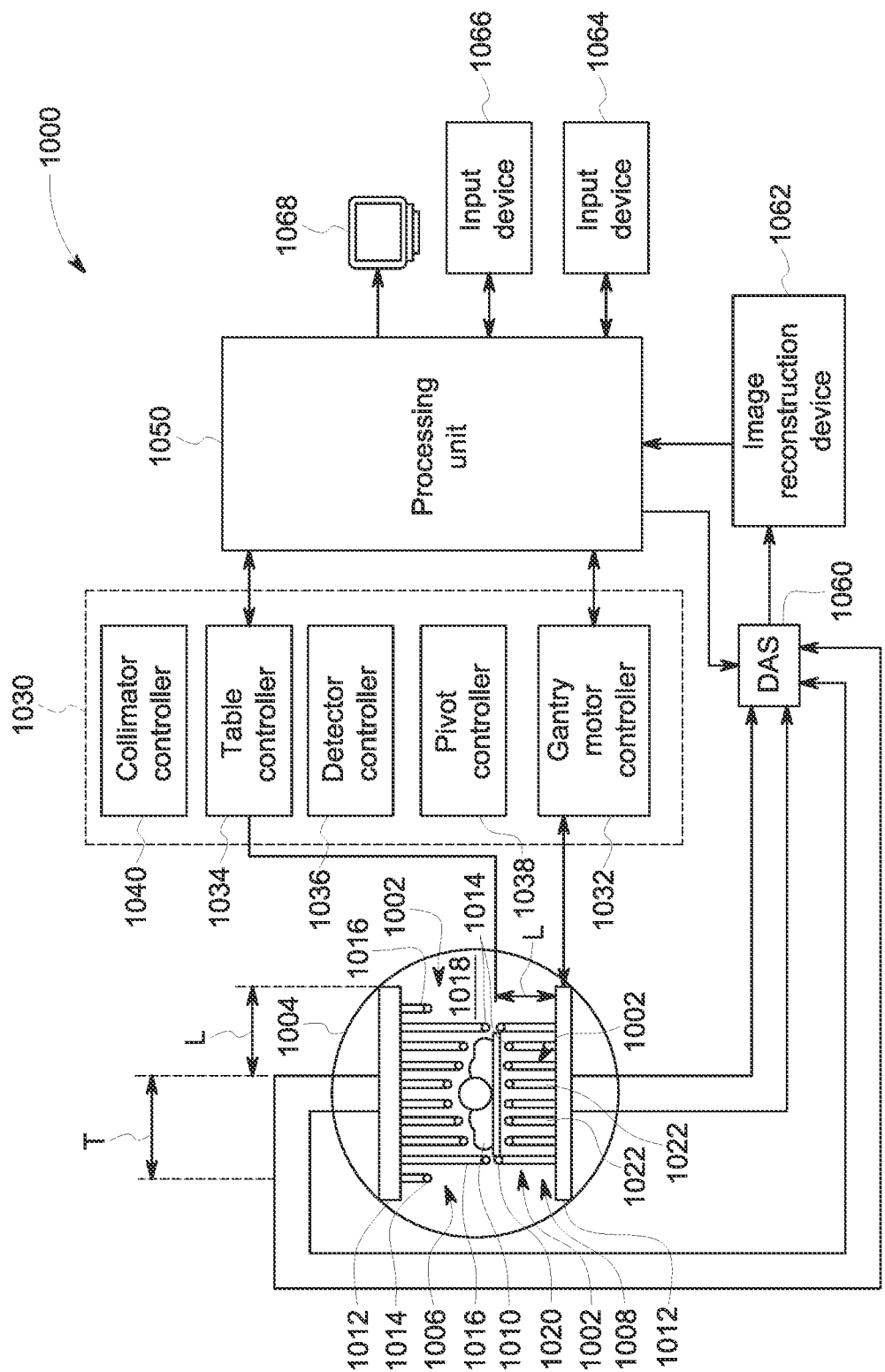
FIG. 8 is a schematic view of an imaging system, in accordance with aspects of the disclosed techniques.

Embodiments described herein may be implemented in medical imaging systems, such as, for example, SPECT and SPECT-CT. Various methods and/or systems (and/or aspects thereof) described herein may be implemented using a medical imaging system. For example, FIG. 8 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 8 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 8. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 8). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly. Each of the imaging detectors 1002 has a radiation detection face, which is directed towards the subject 1010 or a region of interest within the subject.

The collimators 1022 (and detectors) in FIG. 8 are depicted for ease of illustration as single collimators in each detector head. As noted above, in certain embodiments, each detector unit 1014 (or detector head) includes a detector column that be rotated between two different collimators configured for two different energy applications (e.g., high energy versus low energy). Optionally, for embodiments employing one or more parallel-hole collimators, multi-bore collimators may be constructed to be registered or semi-registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, and 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow. In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may rotate a detector column between two different collimators configured for two different energy applications (e.g., high energy versus low energy).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector array 1006 and 1008, which as illustrated in FIG. 8 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as X-ray CT data. In some embodiments, a multi-modality imaging system may be provided, for example, to allow performing NM or SPECT imaging, as well as X-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

In certain embodiments, the radiation shield of the detector column may be constructed to eliminate or minimize radiation penetration to the detector (e.g., CZT modules) outside of the desired areas while providing a compacted shielded enclosure. In addition, in certain embodiments, the radiation shield of the detector column may be configured to be split into two parts to provide easy access for service of detector modules. FIGS. 9-26 provide different detector shielding arrangements relative to the electronics of the detector column.

Figure 9:
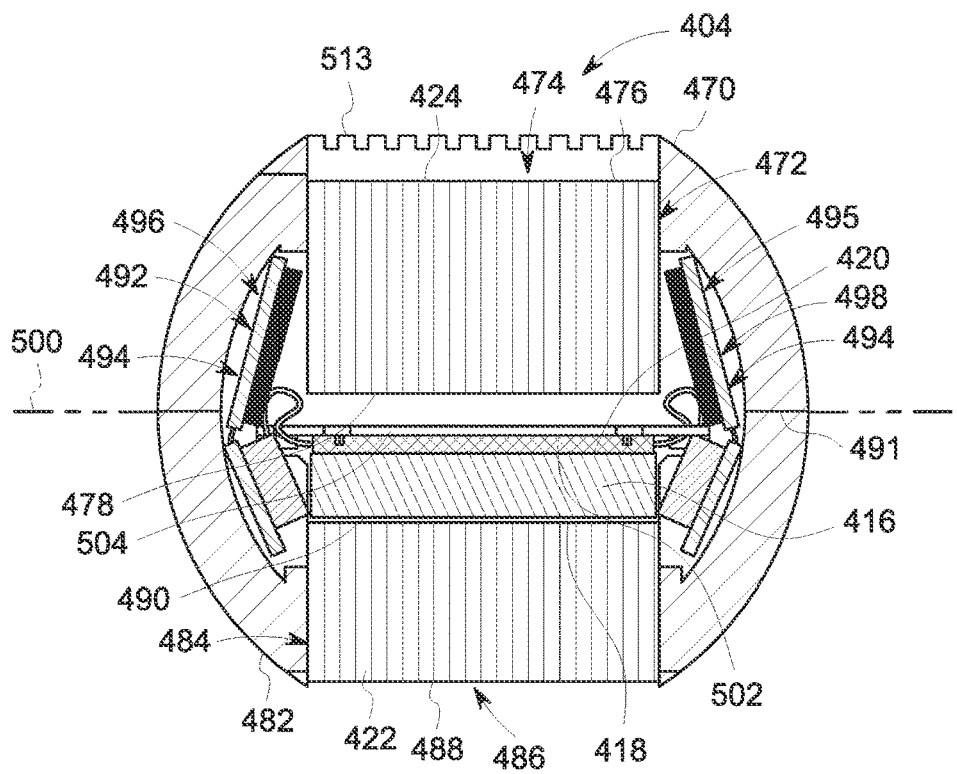
FIG. 9 is a cross-sectional view of a detector column, in accordance with aspects of the disclosed techniques.
Figure 10:
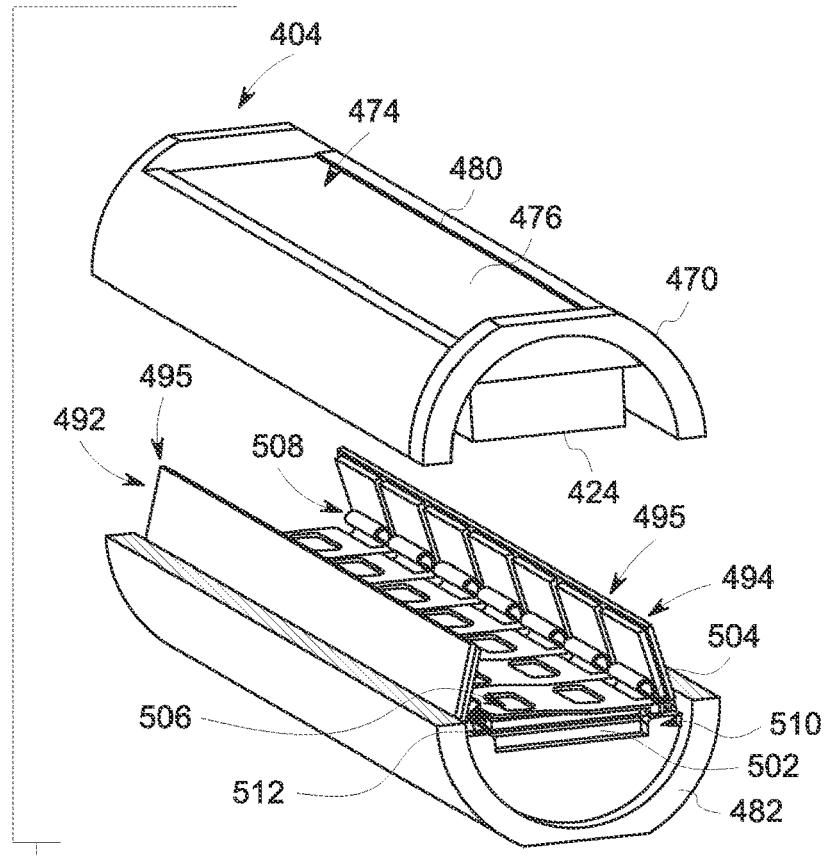
FIG. 10 is a perspective view of the detector column in FIG. 9 (e.g., with a top radiation shield and collimator separated from the detector head)
Figure 11:
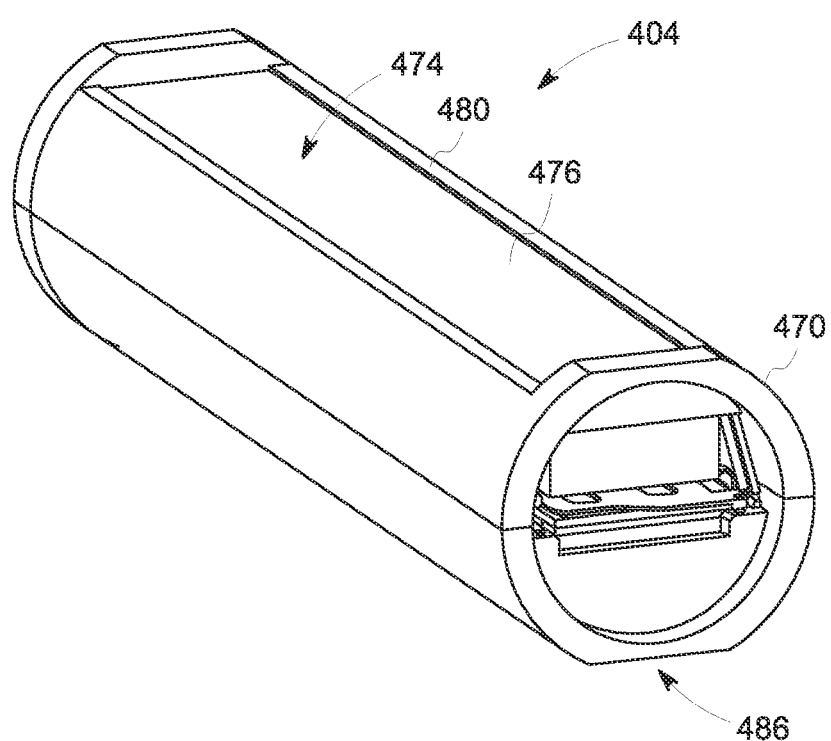
FIG. 11 is a perspective view of the detector column in FIG. 9, in accordance with aspects of the disclosed techniques.

FIG. 9 is a cross-sectional view of the detector column 404. The detector column 404 has a similar structure to the detector column 404 in FIG. 5. For example, the detector column 404 includes the detector 416 (e.g., semiconductor detector such as CZT detector). The detector 416 includes the first surface 418 having a cathode disposed on it and the second surface 420 having pixelated anodes disposed on it. The detector column 404 includes the collimators 422, 424 disposed over both the first surface 418 and the second surface 420 of the semiconductor device 416, respectively. The collimator 422 disposed over the cathode is configured for utilization during an imaging scan involving radiation in a first energy range (e.g., low energy range of approximately 40 to 300 keV). The collimator 424 disposed over the pixelated anodes is configured for utilization during an imaging scan involving radiation in a second energy range (e.g., high energy range of approximately 250 to 400 keV)

different from the first energy range. The terms "high" and "low" as utilized herein are relative, with high energy meaning an energy higher than another energy and low energy meaning an energy lower than another energy. As noted above, the first and second energy ranges may partially overlap (e.g., at a high end of the first energy range and a low end of the second energy range) but differ in extent. As noted above, the collimators 422, 424 may be utilized during the same scan involving dual isotopes (e.g., high and low energy isotopes). The heights of the collimators 422, 424 may be as described in FIG. 5.

The detector column 404 includes a first radiation shield 470 (e.g., top radiation shield) disposed over the collimator 424. The first radiation shield 470 includes a recess 472 for receiving (and holding) the collimator 424 to enable the integration of the collimator 424 into the first radiation shield 470. The first radiation shield 470 also includes an opening 474 disposed over and extending along a surface 476 of the collimator 424. The surface 476 is opposite the surface 420 of the detector 416 (and a surface 478 that interfaces with the surface 420). The first radiation shield 470 extends around perimeter 480 of the surface 476. The first radiation shield 470 also flanks the collimator 424 along its longitudinal length.

The detector column 404 includes a second radiation shield 482 (e.g., bottom radiation shield) disposed over the collimator 422. The second radiation shield 482 includes a recess 484 for receiving (and holding) the collimator 422 to enable the integration of the collimator 422 into the second radiation shield 482. The second radiation shield 482 also includes an opening 486 disposed over and extending along a surface 488 of the collimator 422. The surface 488 is opposite the surface 418 of the detector 416 (and a surface 490 that interfaces with the surface 420). The second radiation shield 482 extends around a perimeter of the surface 488. The second radiation shield 482 also flanks the collimator 422 along its longitudinal length. The first radiation shield 470 and the second radiation shield 482 abut each other at interface 491 to enclose the detector 416 and the collimators 422, 424. The radiation shields 470, 482 may be made of lead. In certain embodiments, the radiation shields 470, 482 may be an aluminum extrusion having lead. In certain embodiments, the radiation shields may be made of tungsten-filled polymer.

One of radiation shields 470, 482 is coupled to a pivoting shaft that enables rotation of the detector column 404. In certain embodiments, the first radiation shield 470 may be coupled to the pivoting shaft. In certain embodiments, the second radiation shield 482 may be coupled to the pivoting shaft.

Respective sets 492, 494 of printed circuit boards 495 having digital electronics (e.g., power boards, digital readout boards) are located in respective cavities 496, 498 formed between the radiation shields 470, 482, the collimators 422, 424, and the semiconductor detector 416. The sets 492, 494 of printed circuit boards 495 flank both portions of the collimator 422, 424 and the semiconductor detector 416. The sets 492, 494 of printed circuit boards 495 are disposed at oblique angles (see FIG. 9) relative to a plane 500 along the interface 491 to provide more space for connectors and to enable removal of detector modules. The positioning of the sets 492, 494 of printed circuit boards 495 reduces interference due to non-detecting material. In particular, no interfering material is located on the backside (e.g., anode side) to enable gamma ray collection from both the back and front sides of the detector 416. The printed circuit boards 495, may include dedicated routing blocks and field programmable gate arrays.

A printed circuit board 502 including an analog front-end including data channels and ASICs is disposed between the collimator 422 and the semiconductor detector 416. The analog electronics on the printed circuit board 502 are coupled to the digital electronics on the sets 492, 496 of printed circuit boards 495. A structure 504 (e.g., made of aluminum, brass, or graphene) is disposed between the collimator 424 and the printed circuit board 502. The structure 504 acts as a heat sink to transfer heat. The structure 504 is glued to the ASICs on the analog front-end on the printed circuit board 502. The structure 504 also includes fiducial points for collimator registration. In particular, the structure 504 includes hole features 506 and slot features 508 for aligning the structure 504 with the detector modules. The structure 504 also includes holes 510 that align with holes 512 in the second radiation shield 482. Pins may be disposed within the aligned holes 510, 512.

Besides the structure 504 acting as a heat sink, each collimator 422, 424 enables heat removal from the detector column 404. For example, the collimators 422, 424 enable heat removal from the analog ASIC associated with each detector module at approximately 2 Watt per module (e.g., 14 Watt total for 7 detector modules). In certain embodiments, the detector column includes a heat sink 513 disposed over surface 476 of the collimator 424. The heat sink 513 may be made from aluminum, brass, or graphene to minimize attenuation. The heat dissipation flow occurs from the detector 416 (e.g., detector modules) to the structure 504 to the collimator 424 and then to heat sink 513.

Figure 12:
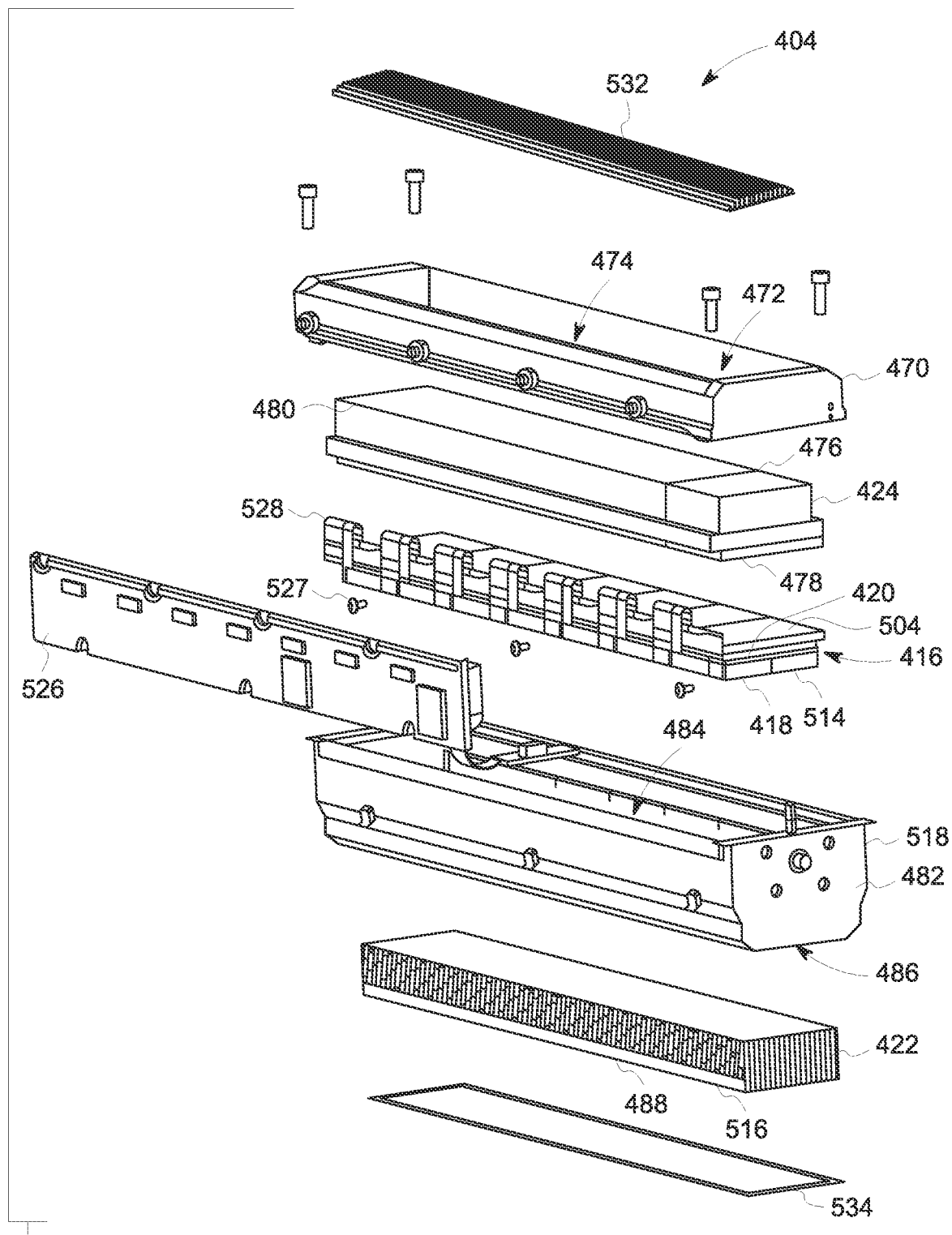
FIG. 12 is an exploded perspective view of a detector column, in accordance with aspects of the disclosed techniques.
Figure 13:
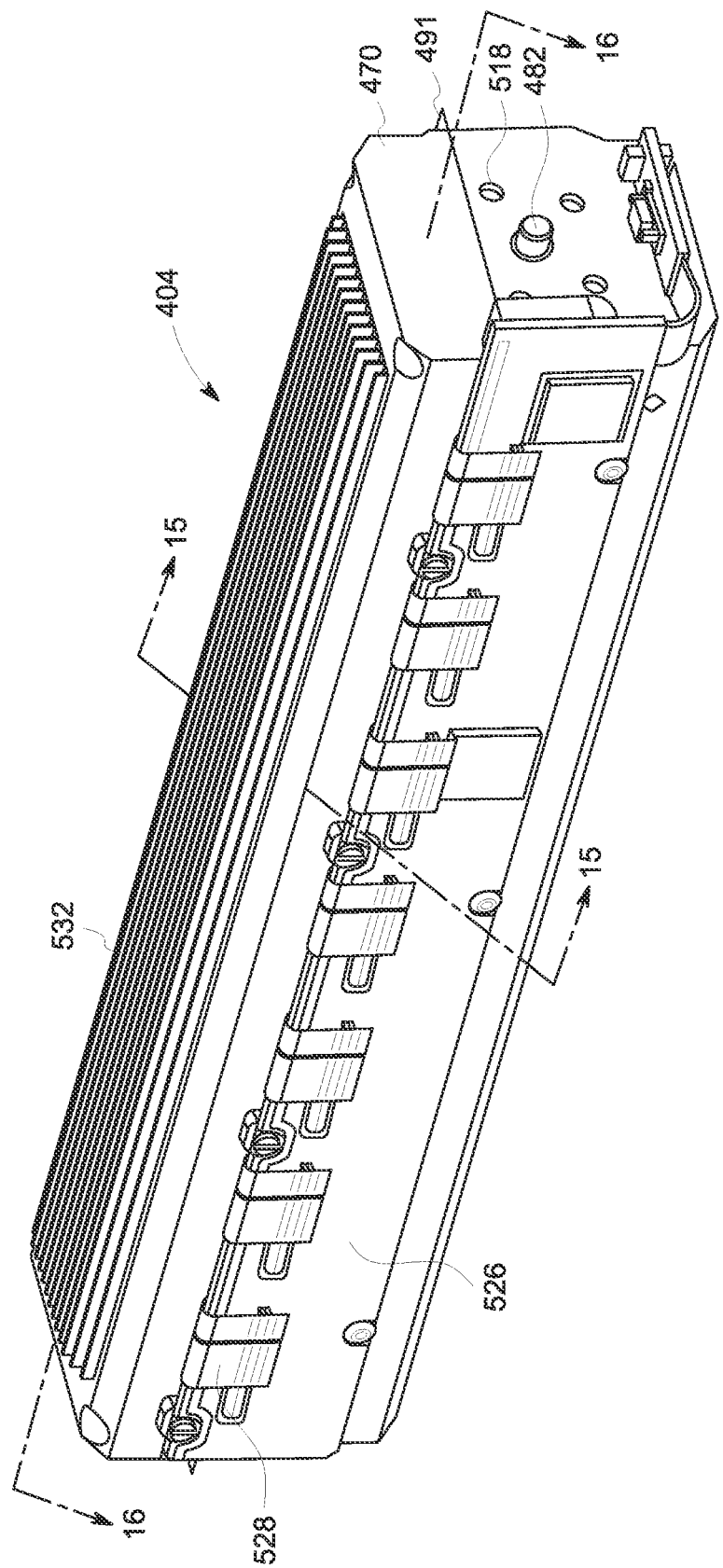
FIG. 13 is a perspective view of the detector column in FIG. 12, in accordance with aspects of the disclosed techniques.
Figure 14:
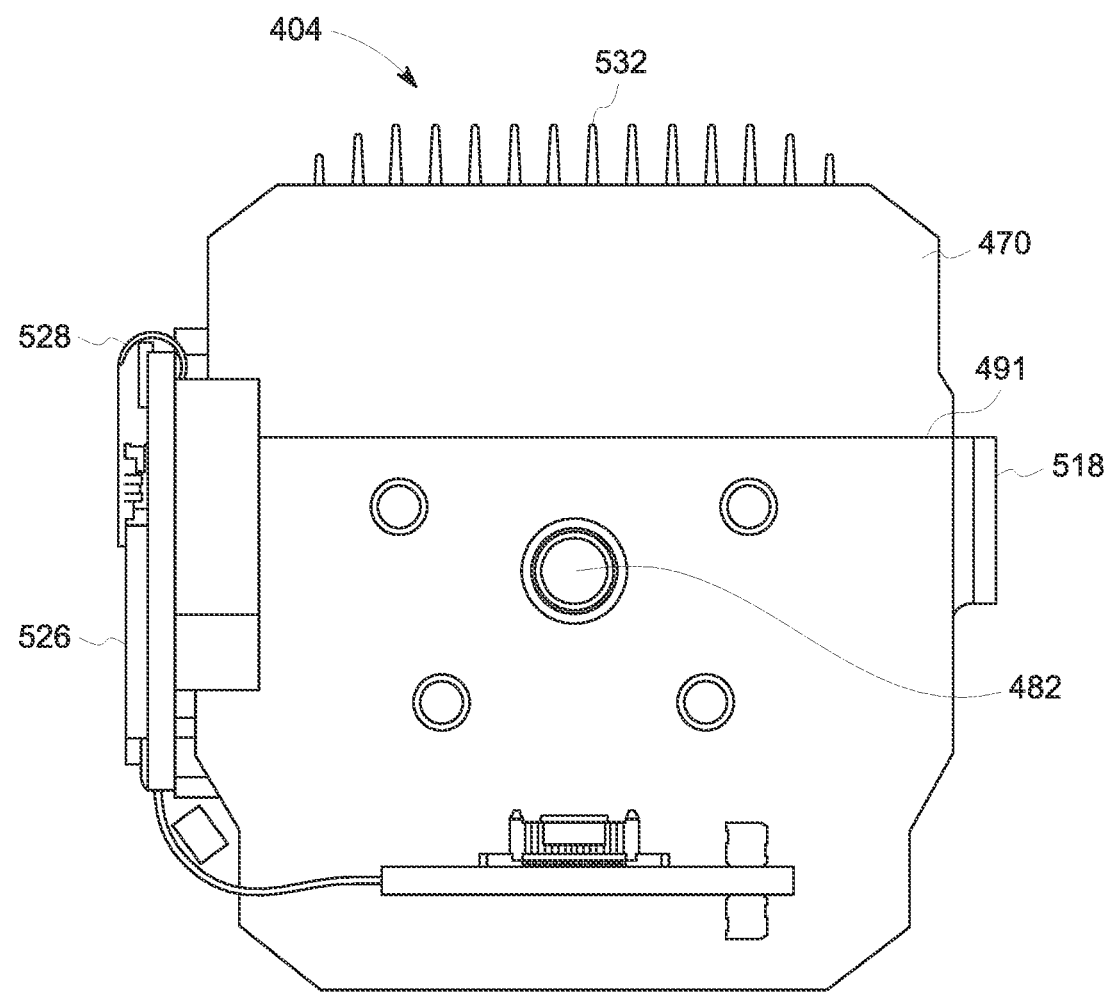
FIG. 14 is end view of the detector column in FIG. 12, in accordance with aspects of the disclosed techniques.
Figure 15:
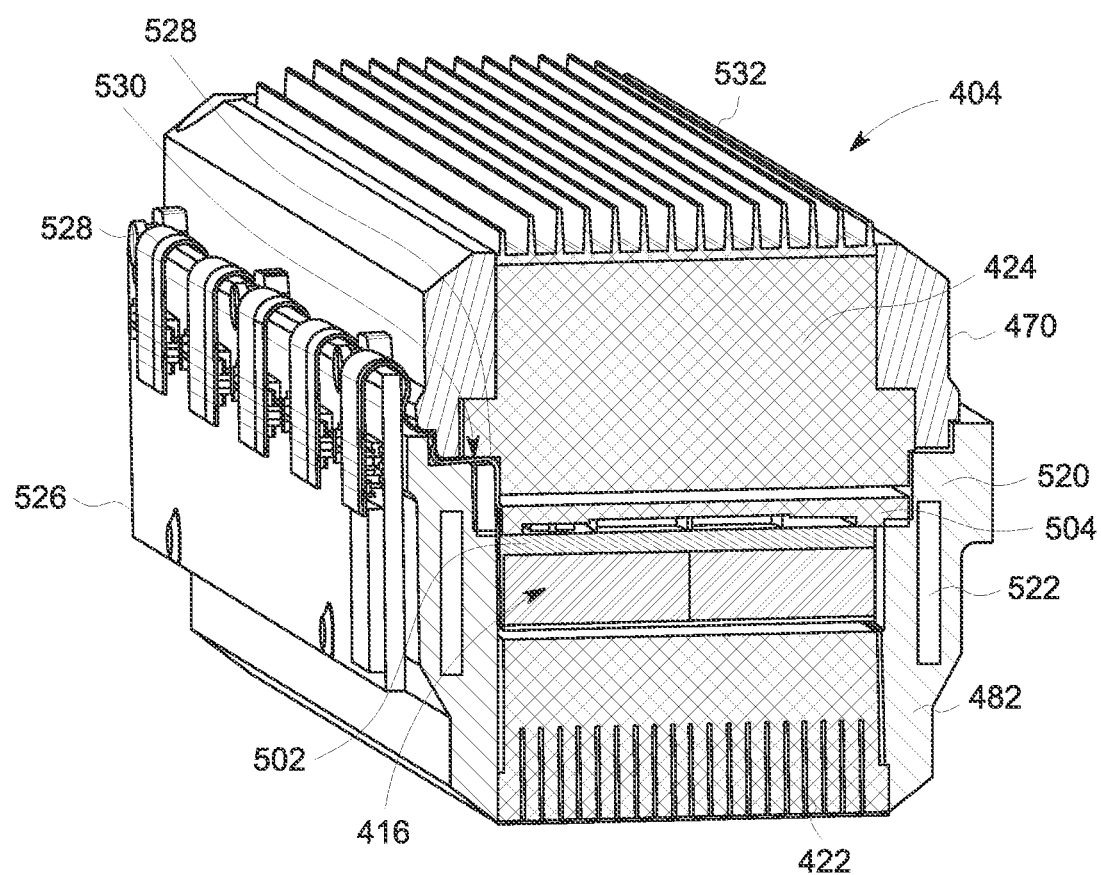
FIG. 15 is a cross-sectional view of the detector column in FIG. 12, taken along line 15-15 in FIG. 13, in accordance with aspects of the disclosed techniques.
Figure 16:
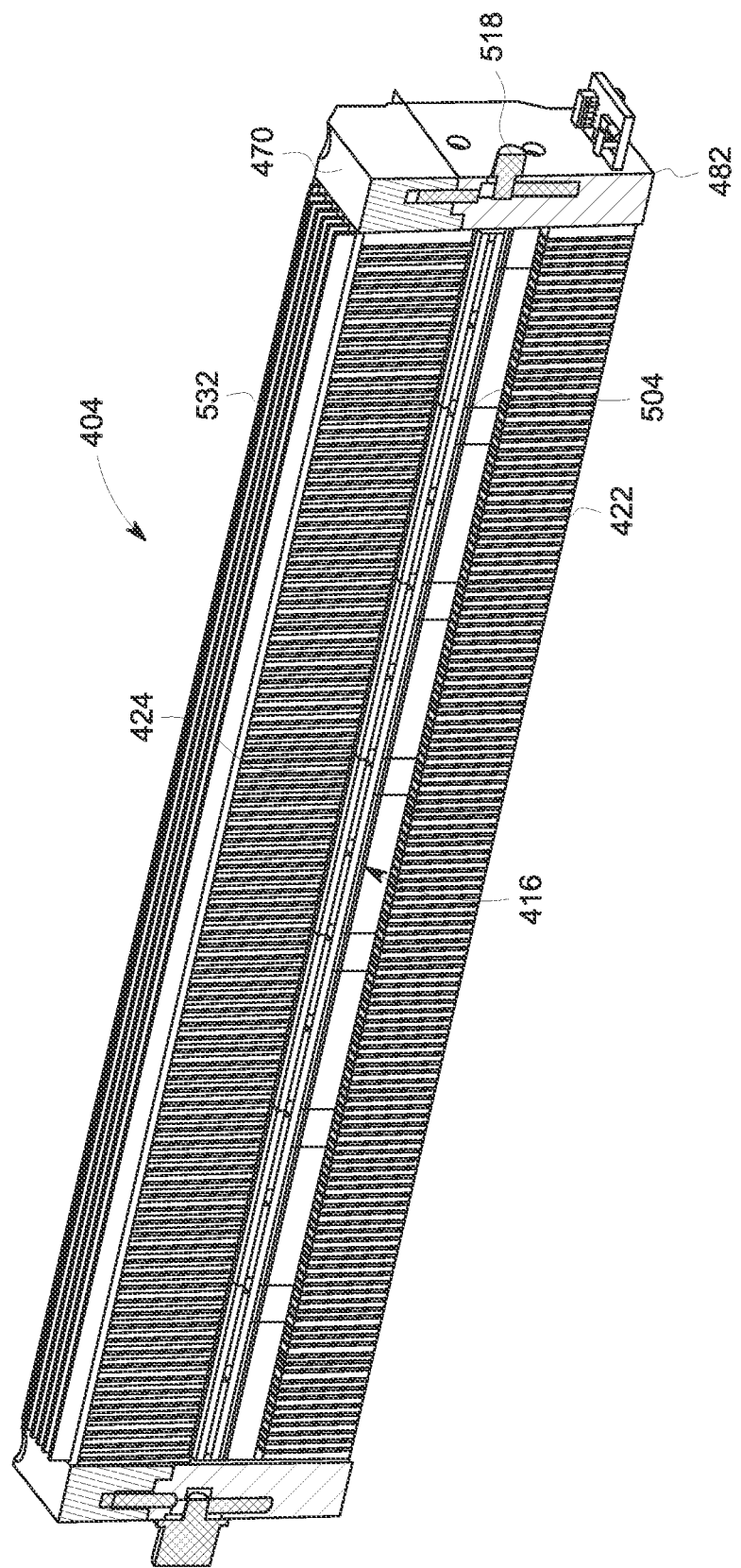
FIG. 16 is a cross-sectional view of the detector column in FIG. 12, taken along line 16-16 in FIG. 13, in accordance with aspects of the disclosed techniques.

FIG. 12 is an exploded perspective view of an alternative detector column 404. FIGS. 13 and 14 are perspective and end views, respectively, of the detector column 404 in FIG. 12. FIGS. 15 and 16 are cross-sectional views of the detector column 404 in FIG. 12. The detector column 404 has a similar structure to the detector column 404 in FIG. 5. For example, the detector column 404 includes the detector 416 (e.g., semiconductor detector such as CZT detector). The detector 416 includes multiple detector modules 514 (e.g., CZT detector modules). As depicted, the detector includes 7 detector modules 514. The number of detector modules 514 may vary. The detector 416 includes the first surface 418 having a cathode disposed on it and the second surface 420 having pixelated anodes disposed on it. The detector column 404 includes the collimators 422, 424 disposed over both the first surface 418 and the second surface 420 of the semiconductor device 416, respectively. The collimator 422 disposed over the cathode is configured for utilization during an imaging scan involving radiation in a first energy range (e.g., low energy range of approximately 40 to 300 keV). The collimator 424 disposed over the pixelated anodes is configured for utilization during an imaging scan involving radiation in a second energy range (e.g., high energy range of approximately 250 to 400 keV) different from the first energy range. The terms "high" and "low" as utilized herein are relative, with high energy meaning an energy higher than another energy and low energy meaning an energy lower than another energy. As noted above, the first and second energy ranges may partially overlap (e.g., at a high end of the first energy range and a low end of the second energy range) but differ in extent. As noted above, the collimators 422, 424 may be utilized during the same scan involving dual isotopes (e.g., high and low energy isotopes). The heights of the collimators 422, 424 may be as described in FIG. 5.

The detector column 404 includes a first radiation shield 470 (e.g., top radiation shield) disposed over the collimator 424. The first radiation shield 470 includes a recess 472 for receiving (and holding) the collimator 424 to enable the integration of the collimator 424 into the first radiation shield 470. The first radiation shield 470 also includes an opening 474 disposed over and extending along a surface 476 of the collimator 424. The surface 476 is opposite the surface 420 of the detector 416 (and a surface 478 that interfaces with the surface 420). The first radiation shield 470 extends around perimeter 480 of the surface 476. The first radiation shield 470 also flanks the collimator 424 along its longitudinal length.

The detector column 404 includes a second radiation shield 482 (e.g., bottom radiation shield) disposed over the collimator 422. The second radiation shield 482 includes a recess 484 for receiving (and holding) the collimator 422 to enable the integration of the collimator 422 into the second radiation shield 482. The second radiation shield 482 also includes an opening 486 disposed over and extending along a surface 488 of the collimator 422. The surface 488 is opposite the surface 418 of the detector 416 (and a surface 490 that interfaces with the surface 420). The second radiation shield 482 extends around a perimeter 516 of the surface 488. The second radiation shield 482 also flanks the collimator 422 along its longitudinal length. The first radiation shield 470 and the second radiation shield 482 abut each other at interface 491 to enclose the detector 416 and the collimators 422, 424. The first radiation shield 470 and the second radiation shield 482 are coupled together via fasteners 517 (e.g., bolts) disposed within openings (on radiation shields 470, 482) for receiving the fasteners 517.

One of radiation shields 470, 482 is coupled to a pivoting shaft that enables rotation of the detector column 404. In certain embodiments, the first radiation shield 470 may be coupled to the pivoting shaft. In certain embodiments (as depicted in FIGS. 12-14), the second radiation shield 482 is coupled to a pivoting shaft 518. Only a portion of the pivoting shaft 518 is shown.

The first radiation shield 470 may be made of lead. In certain embodiments, the first radiation shield 470 may be an aluminum extrusion having lead. The second radiation shield 482 may be made of tungsten-filled polymer 520 overmolded on one or more tungsten plates 522 as depicted in FIG. 15. As depicted in FIG. 15, the tungsten plates 522 may flank the detector 416.

Figure 17:
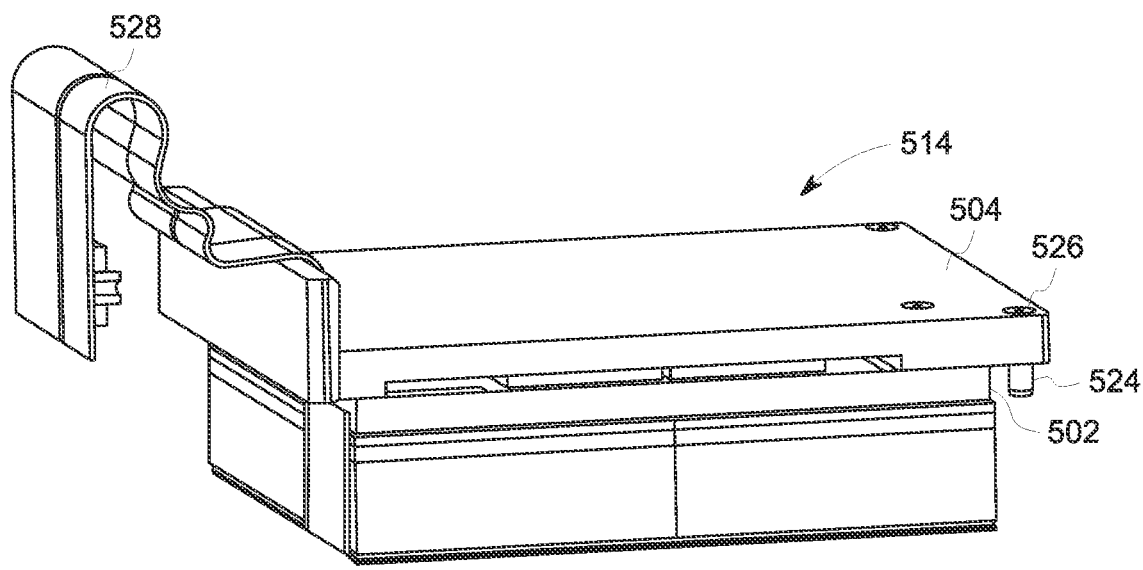
FIG. 17 is a detector module with a flex circuit, in accordance with aspects of the disclosed techniques.
Figure 18:
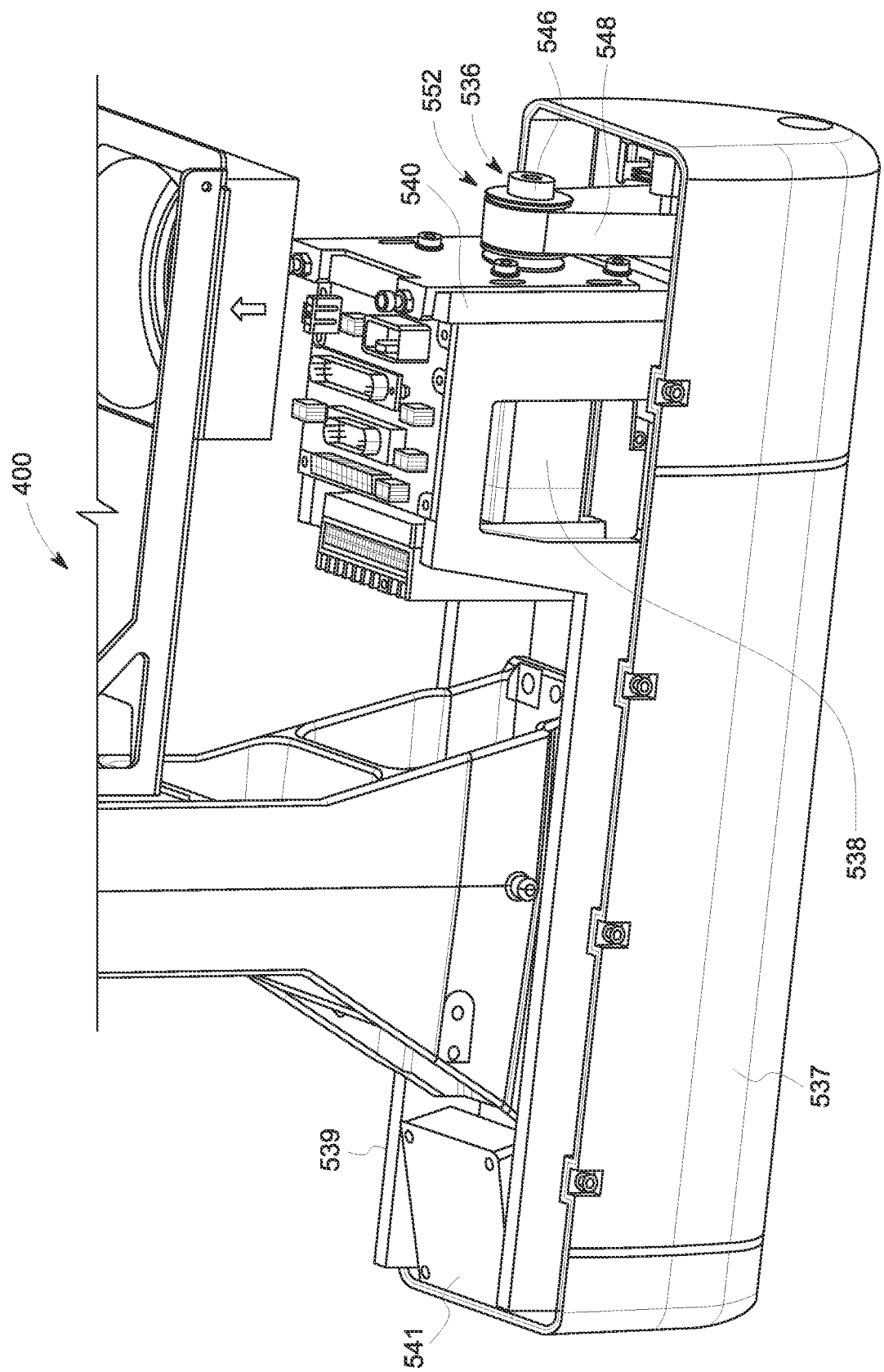
FIG. 18 is a perspective view of a detector head (e.g., having a cover), in accordance with aspects of the disclosed techniques.

Each detector module 514 (as depicted in FIG. 17) includes a printed circuit board 502 including an analog front-end including data channels and ASICs disposed on the side of the detector 416 between the collimator 422 and the semiconductor detector 416. Each detector module 514 includes a structure 504 (e.g., made of aluminum, brass, or graphene) disposed between the collimator 424 and the printed circuit board 502. The structure 504 acts as a heat sink to transfer heat. The structure 504 is glued to the ASICs on the analog front-end on the printed circuit board 502. The structure 504 also includes fiducial points (e.g., pins 524) for collimator registration. In particular, the structure 504 includes one or more holes 526 for receiving respective pins 524. A cross-sectional profile of the structure 504 in FIG. 17 varies from the structure 504 in FIGS. 9 and 10.

The detector column 404 incudes a module board 526 having digital electronics (e.g., power boards, digital readout boards). The module board 526 may include dedicated routing blocks and field programmable gate arrays. The module board 526 having the digital electronics is disposed outside of the radiation shields 470, 482. As depicted, the module board 526 is disposed on a single side of the detector column 404 along the longitudinal length of the detector column 404. In certain embodiments, a respective module board 526 having digital electronics may be disposed on both sides of the detector column 404 along the longitudinal length of the detector column. The module board 526 may be coupled to the second radiation shield via fasteners 527 disposed in corresponding openings for the module board 526 and the second radiation shield 482 for receiving the fasteners 527. The detector module 514 incudes a flex circuit or flex cable 528 coupled to the analog electronics that couples to the module board 526 (and the digital electronics) outside of the radiation shields 470, 482. The flex circuits 528 of the detectors modules extend through a labyrinth 530 (as depicted in FIG. 15) formed by the radiation shields 470, 482. Having the module board 526 outside the radiation shields 470, 482 reduces interference due to non-detecting material.

The detector column 404 includes a heat sink 532 disposed within and extending across the opening 474. The heat sink 532 is transparent to high energy radiation. The heat sink 532 may be made of aluminum, brass, or graphene to minimize attenuation. The heat dissipation flow occurs from the detector 416 (e.g., detector modules 514) to the structure 504 to the collimator 424 and then to heat sink 532. A cover 534 is disposed over opening 486 in the second radiation shield 482. The cover 534 acts as a gas seal.

FIGS. 18-21 are different perspective views of the detector head 400 having the detector column 404 of FIGS. 12-16. The detector head 400 includes a position detection system 536 coupled to the detector column 404. The position detection system 536 is configured to detect a position of a detector column 404 during an imaging sequence. The position detection system 536 and the detector column 404 are housed within a housing or cover 537. The housing 537 is transparent to radiation. The detector column 404 is coupled to a frame 539. A fan 541 is coupled to the frame 539 and is configured to direct cooling air toward the detector column 404.

Figure 22:
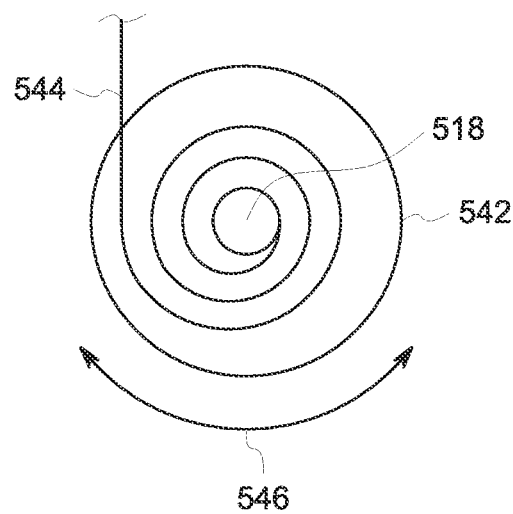
FIG. 22 is a schematic diagram of a flexible conductor disposed about a shaft of a detector column, in accordance with aspects of the disclosed techniques.

The detector head 400 includes a sweep motor 538 coupled to chassis 540 that may be utilized to pivot the detector column 404 about its longitudinal axis (e.g., sweeping axis). The rotating shaft 518 of the detector column 404 is coupled to a housing 542 (e.g., spool or reel). The housing 542 has a flexible conductor 544 (e.g., flexible spiral) wound about the housing 542 similar to a spiral (as depicted in FIG. 22). As depicted in FIG. 22, during rotation of the detector column 404 in direction 546 (e.g., about a rotational axis of the detector column 404), the flexible conductor 544 may unwind from the housing 542 or wind about the housing 542 depending on the direction 546. The flexible conductor 544 enables transfer of signals between the rotating detector column 404 and non-rotating components.

The sweep motor 538 includes a gear 546 coupled to the rotating shaft 518 via a belt 548 disposed about both the gear 546 and a gear 550 coupled to the shaft 518. The gears 546, 550 and the belt 548 form a timing pulley 552 to drive rotation of the detector column 404. The timing pulley 552 forms a part of the position detection system 536.

The position detection system 536 also includes an encoder 554 for providing feedback on the position of the detector column 404. The position detection system 536 also includes a sweep mechanical stopper 556, sweep homing optocouplers 558, a plate 560, and a ball bearing 562. The components of the position detection system 536 are coupled to the chassis 540.

Figure 23:
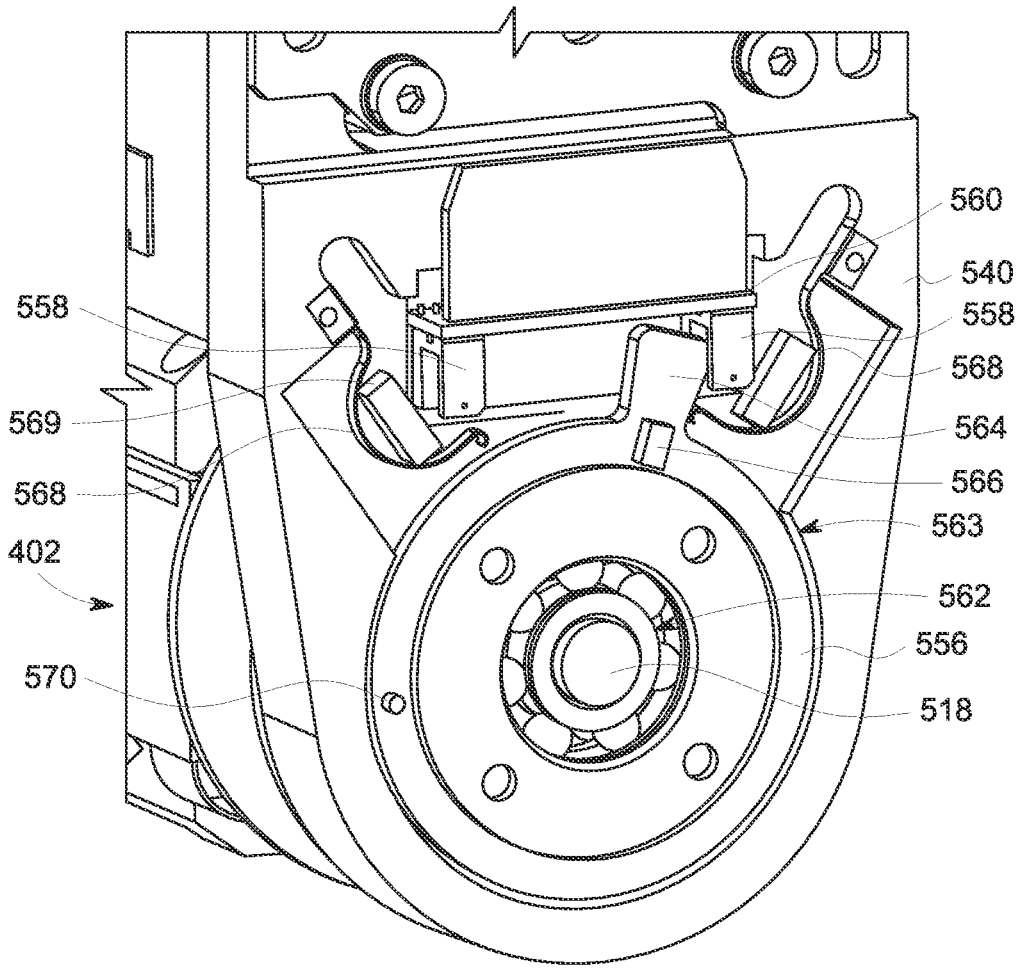
FIG. 23 is a cross-sectional view through a position detection system coupled to the detector column in FIG. 19, taken along line 23-23 in FIG. 19, in accordance with aspects of the disclosed techniques.

The detector column 404 shown in FIGS. 12-16 and 18-21 is configured to rotate greater than 360 degrees about its longitudinal axis. FIG. 23 is a cross-sectional view through the position detection system 536 coupled to the detector column 404 in FIG. 19, taken along line 23-23. As depicted in FIG. 23, the ball bearing 562 is disposed about the shaft 518. The plate 560 is coupled to the chassis 540. The sweep mechanical stopper 556 (which is free-swinging) is disposed about the plate 560. The sweep mechanical stopper 556 is partially disposed within a recess 563 on the face of the chassis 540. The sweep mechanical stopper 556 includes a protrusion 564 that extends radially (e.g., relative to a rotational axis of the stopper 556). The sweep mechanical stopper 556 also includes a stopper tooth 566 that extends axially (e.g., in a direction along the rotational axis of the stopper 556).

The protrusion 564 interacts with a pair of sweep homing optocouplers 558 coupled to a printed circuit board 560 and partially disposed within the recess 563 of the chassis 540. During rotation of the sweep mechanical stopper 556 (e.g., clockwise or counterclockwise), the protrusion 564 interacts with one of the optocouplers 558. A pair of leaf springs 568 flanks the optocouplers 558. The pair of leaf springs 568 are partially disposed within the recess 563 of the chassis 540. The respective leaf springs 568 are configured to disengage the sweep mechanical stopper 556 from respective optocouplers 558 as described in greater detail below. A pair of blocks 569 on the chassis 540 flank the optocouplers 558 to limit the range of the sweep mechanical stopper 556 to between the blocks 569 (and the optocouplers 558). The stopper tooth 566 is configured to interact with a pin 570 that extends from the gear 550 of the timing pulley 552 in FIG. 21.

Figure 19:
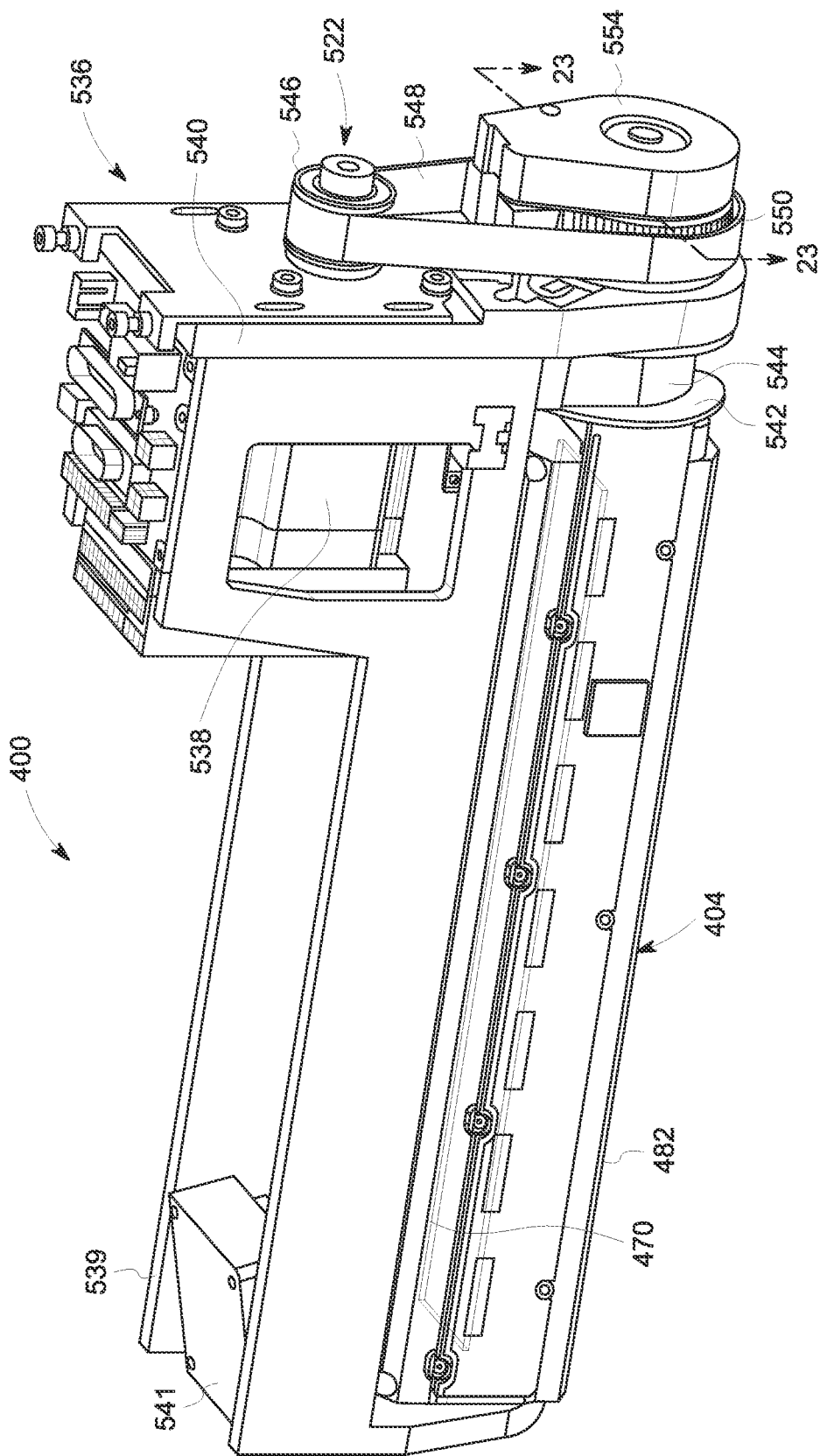
FIGS. 19 and 20 are perspective views of the detector head in FIG. 18 (e.g., without the cover), in accordance with aspects of the disclosed techniques.
Figure 20:
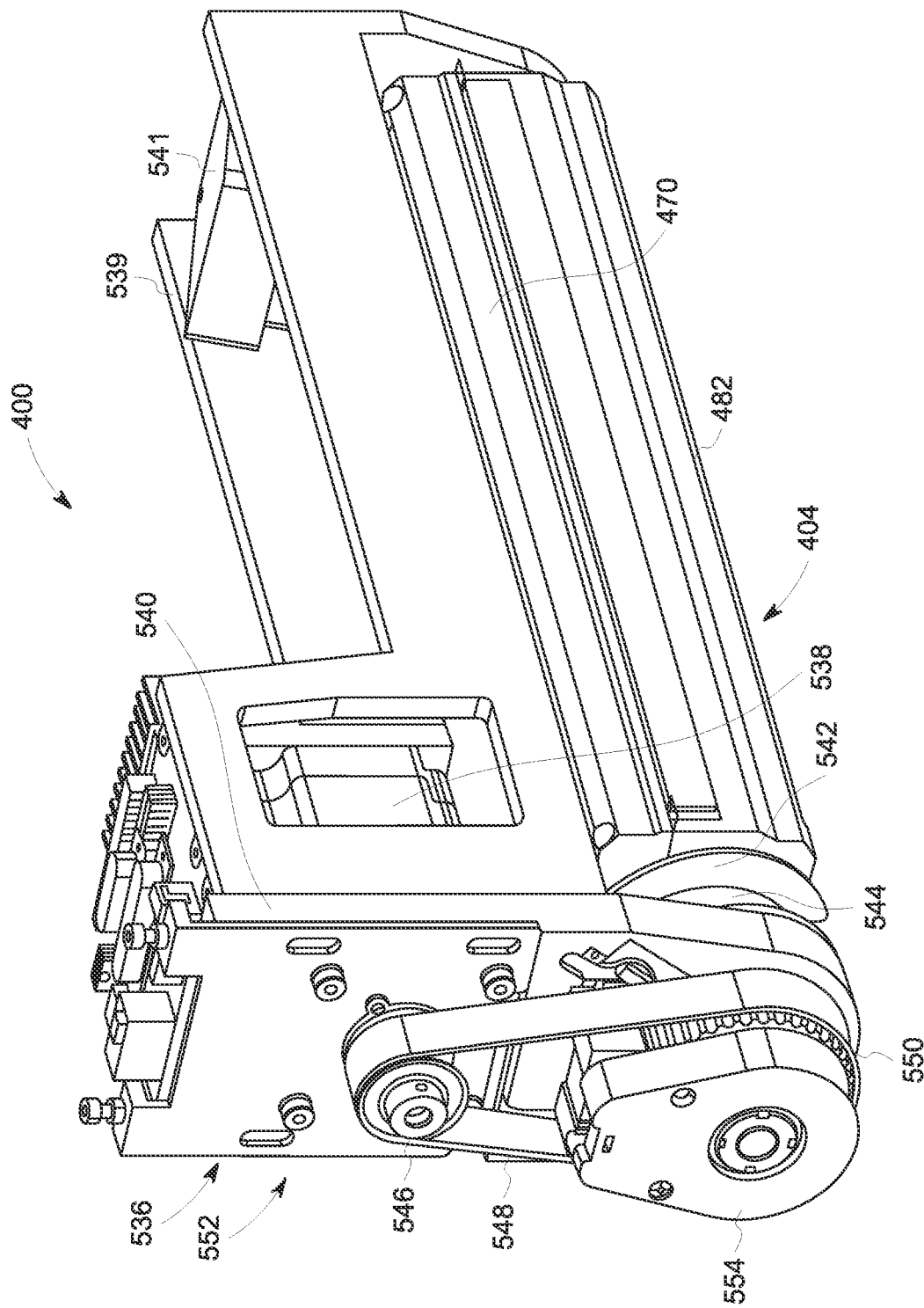
Figure 21:
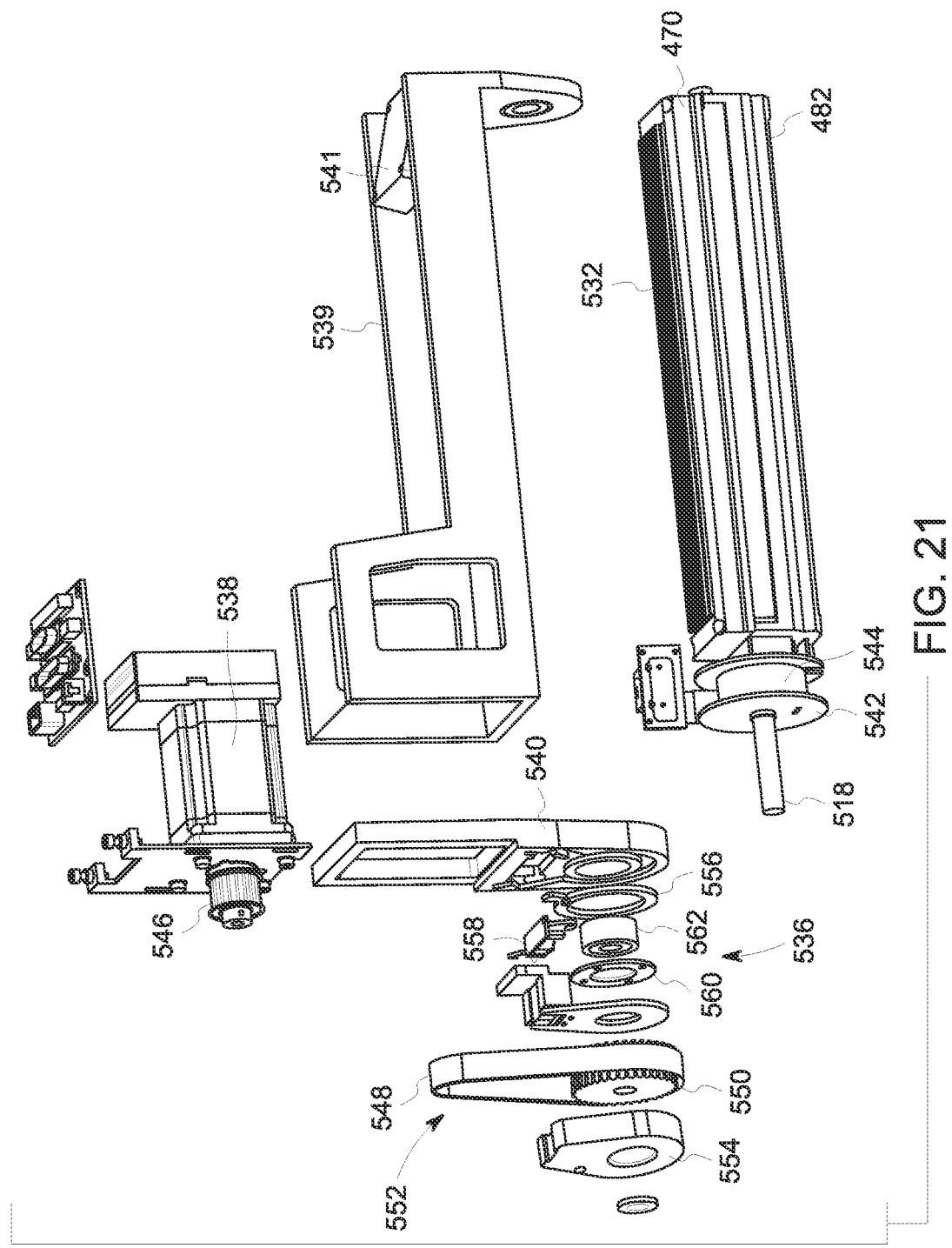
FIG. 21 is an exploded perspective view of the detector head in FIG. 18, in accordance with aspects of the disclosed techniques.
Figure 24:
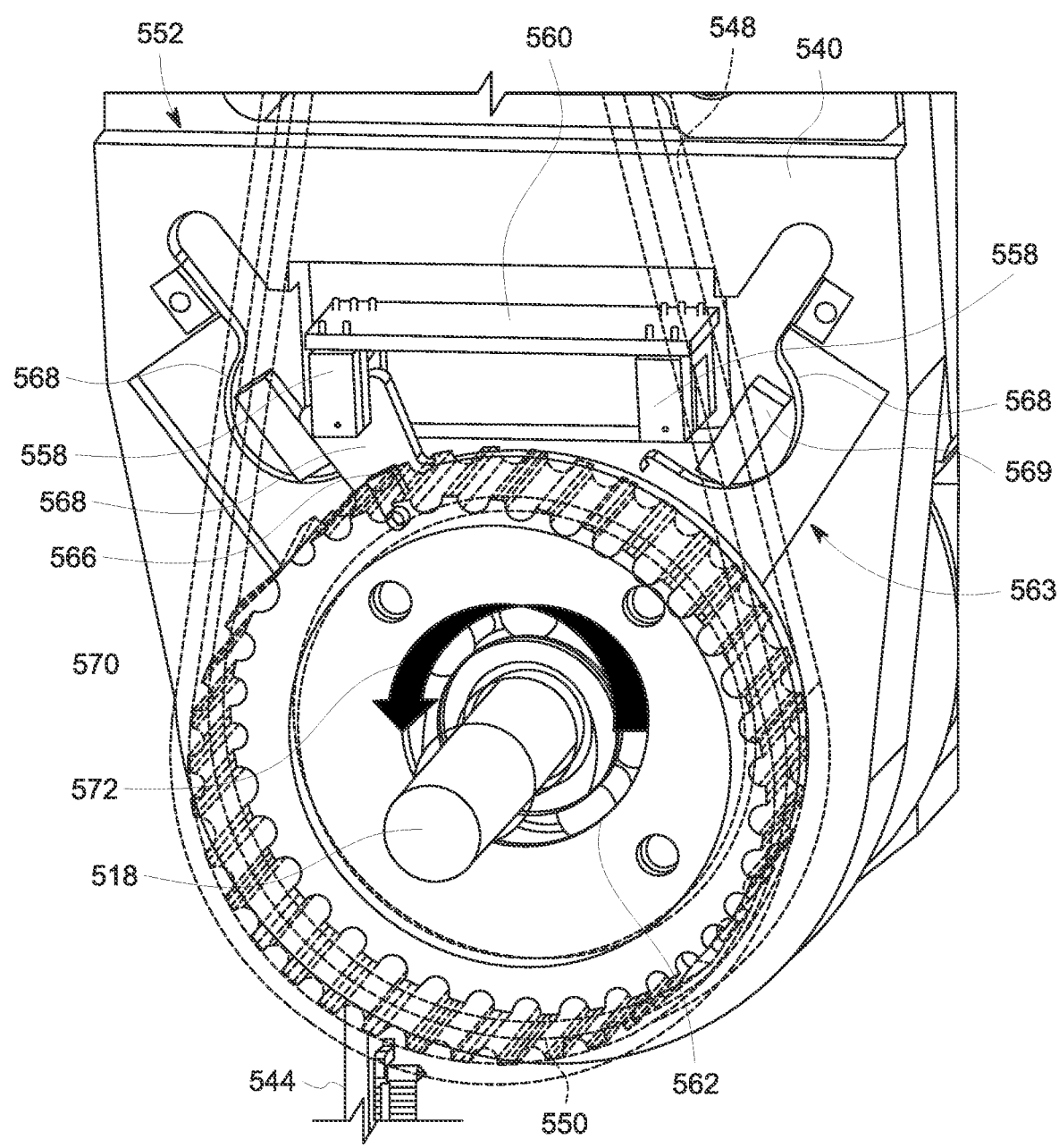
FIGS. 24-26 are perspective views of a portion of the position detection system coupled to the detector column in FIG. 19, in accordance with aspects of the disclosed techniques.
Figure 25:
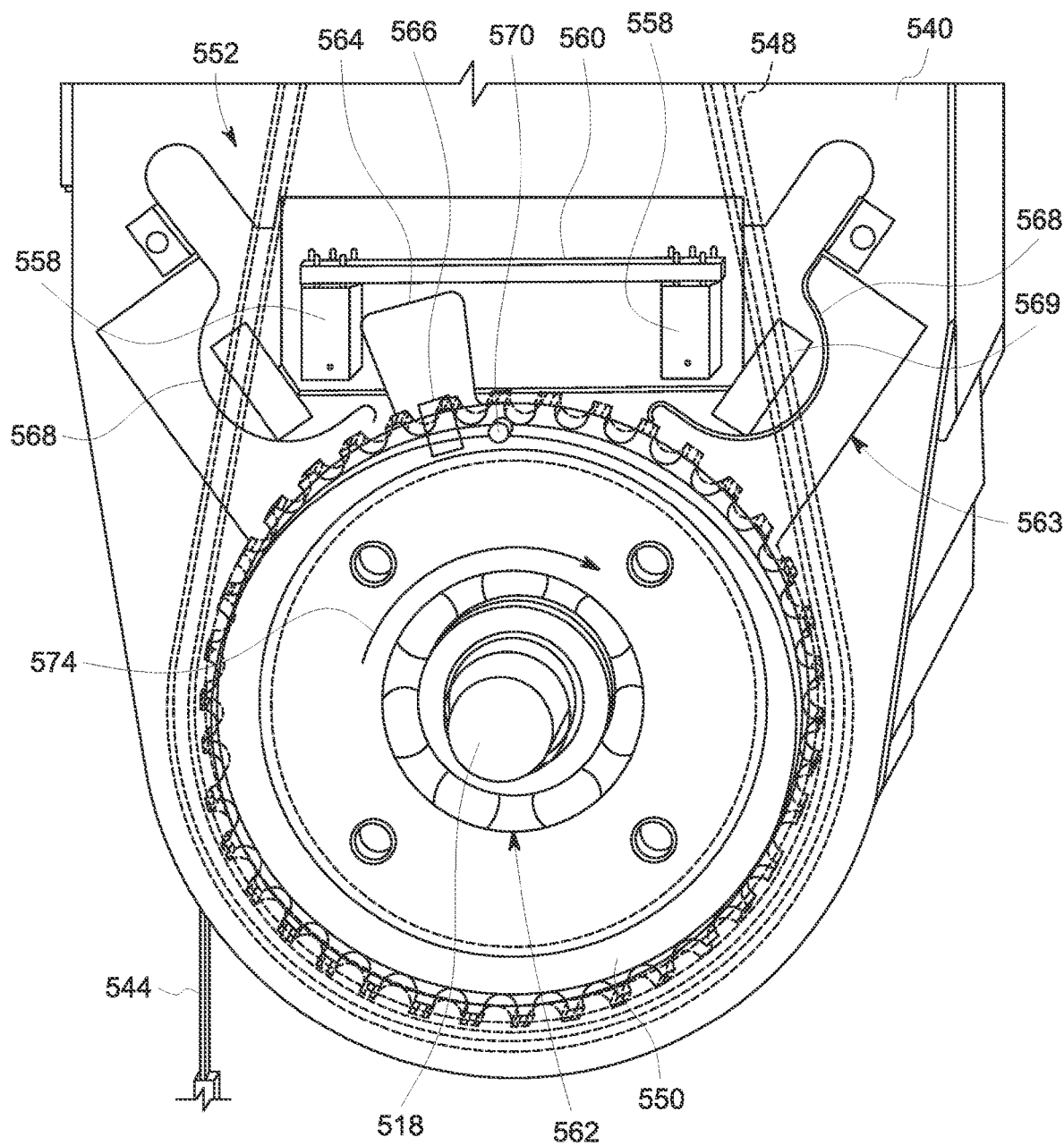
Figure 26:
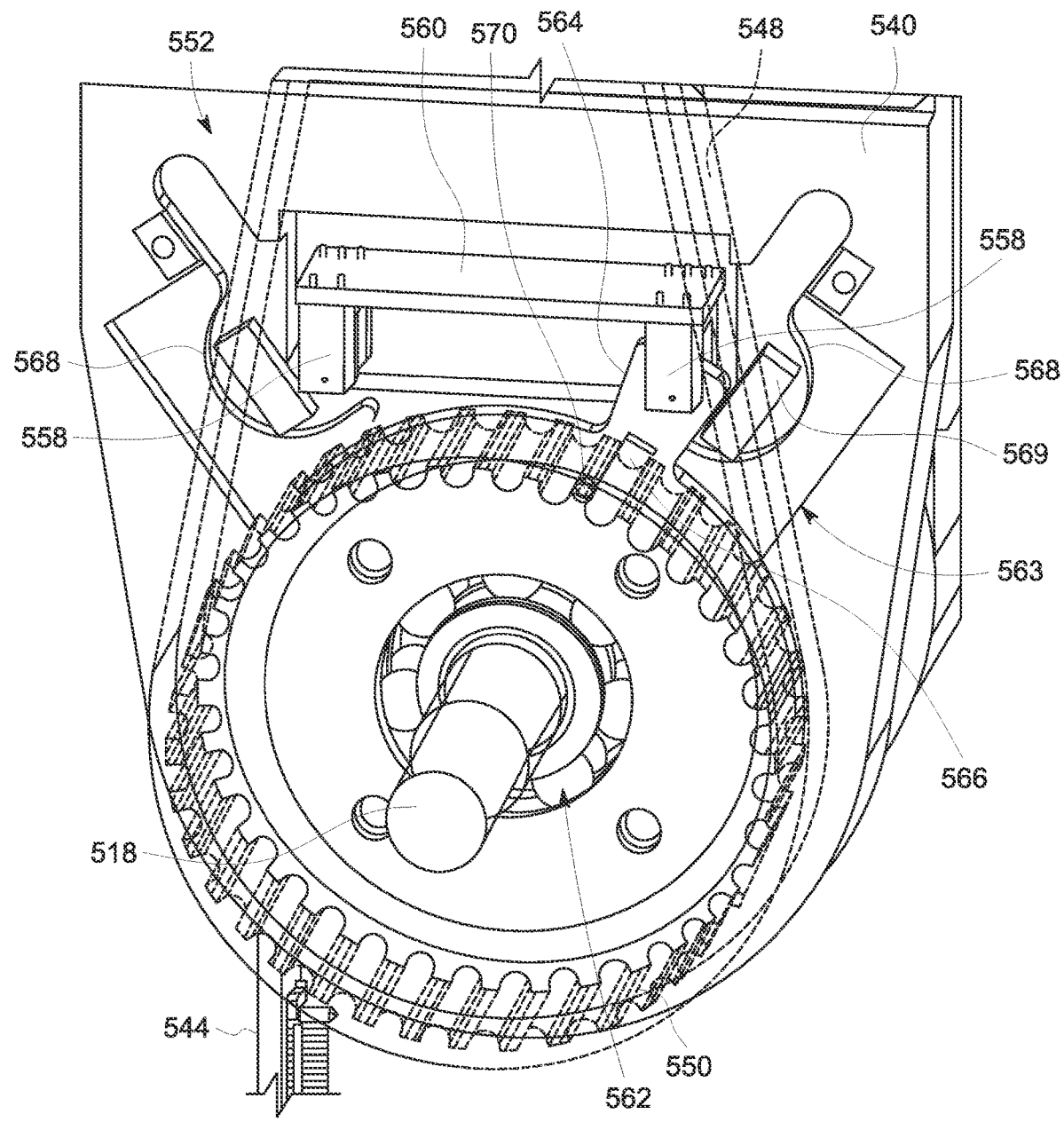

FIGS. 24-26 are perspective views of a portion of the position detection system 536 coupled to the detector column 404 in FIG. 19 that illustrate how various components of the position detection system 536 enable rotation of the detector head that is greater than 360 degrees. References to left and right are relevant to the perspective views shown in FIGS. 24 and 26 and would be reversed if viewing from the opposite end of the detector column 404. As depicted in FIG. 24, after far enough rotation of the gear 550 in a counter-clockwise direction about the rotational axis of the shaft 518 as indicated by arrow 572, the pin 570 interfaces with the right side of the stopper tooth 566 causing the protrusion 564 to briefly interact with the left optocoupler 558. As depicted in FIG. 25, upon the interaction between the protrusion 564 and the left optocoupler 558 (where the left optocoupler 558 is blocked), the left leaf spring 568 exerts a force upon protrusion 564 to disengage the protrusion 564 from the left optocoupler 558 (opening both optocouplers 558) in the clockwise direction about the rotational axis of the shaft 518 as indicated by the arrow 574. In addition, this enables the timing pulley 552 to rotate the gear 550 (and, thus, the detector column 404) in direction 574 until the pin 570 interfaces with the left side of the stopper tooth 566 causing the protrusion 564 to interface with the right optocoupler 558 (and block the right optocoupler 558) as depicted in FIG. 26. The winding and unwinding of the flexible conductor 544 is depicted in FIGS. 24-26 during rotation in the directions 572, 574. From FIGS. 24-26, the gear 540 (as indicated by the pin 570) and, thus, the detector column 404 have rotated greater than 360 degrees in the direction 574 about the sweep axis. The process can be reversed in the opposite direction for the detector head 404 to be rotated greater than 360 degrees in the direction 572 about the sweep axis. In certain embodiments, the sweep rotation range may be greater than 400 degrees (e.g., up to approximately 410 degrees).

Technical effects of the disclosed subject matter include a radiation detector head assembly of a NM multi-head imaging system that includes two collimators (each specifically configured for use with different energy applications such as high and low energy applications). A radiation shield of the detector column is constructed to eliminate or minimize radiation penetration to the detector (e.g., detector modules) outside of the desired areas while providing a compacted shielded enclosure. In addition, in certain embodiments, the radiation shield of the detector column may be configured to be split into two parts to provide easy access for service of detector modules. Further, the detector head is configured to rotate greater than 360 degrees (e.g., about a sweep axis) due to a unique mechanical stopping mechanism.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radiation detector head assembly, comprising:
a detector column, comprising:
   a detector having a first surface and a second surface opposite the first surface;
   a first collimator disposed over the first surface of the detector configured for use during imaging scans involving radiation in a first energy range;
   a second collimator disposed over the second surface of the detector configured for use during imaging scans involving radiation in a second energy range different from the first energy range;
   a first radiation shield disposed over the first collimator, wherein the first radiation shield comprises a first recess for receiving the first collimator and a first opening over a third surface of the first collimator, the third surface being opposite the first surface of the detector; and
   a second radiation shield disposed over the second collimator, wherein the second radiation shield comprises a second recess for receiving the second collimator and a second opening over a fourth surface of the second collimator, the fourth surface being opposite the second surface of the detector.

2. The radiation detector head assembly of claim 1, wherein the first surface of the detector comprises a cathode and the second surface of the detector comprises pixelated anodes.

3. The radiation detector head assembly of claim 2, wherein the detector column comprises a shaft coupled to the second radiation shield that is configured to be rotated to rotate the detector column.

4. The radiation detector head assembly of claim 2, wherein the detector column comprises a heat sink disposed within the first opening.

5. The radiation detector head assembly of claim 2, wherein the detector column comprises a cover disposed within the second opening, wherein the cover is configured to act as a gas seal.

6. The radiation detector head assembly of claim 2, wherein the second radiation shield comprises tungsten-filled polymer overmolded on one or more tungsten plates.

7. The radiation detector head assembly of claim 1, wherein the detector column comprises a first set of printed circuit boards having digital electronics and a second set of printed circuit boards having digital electronics disposed within both the first radiation shield and the second radiation shield that flank both the first collimator and the second collimator, and wherein both the first set of the printed circuit boards and second set of the printed circuit boards are arranged at an oblique angle relative to a plane extending between where the first radiation shield and the second radiation shield abut each other.

8. The radiation detector head assembly of claim 1, wherein the detector column comprises a module board having digital electronics disposed outside both the first radiation shield and the second radiation shield.

9. The radiation detector head assembly of claim 8, wherein the detector column comprises flexible circuits extending from analog electronics coupled to the detector to the module board.

10. The radiation detector head assembly of claim 9, wherein the first radiation shield and the second radiation shield form a labyrinth that the flexible circuits extend through to couple to the module board.

11. The radiation detector head assembly of claim 1, wherein the detector column is configured to rotate greater than 360 degrees about its longitudinal axis.

12. The radiation detector head assembly of claim 11, wherein the radiation detector head assembly comprises:
a flexible conductor wrapped around a housing coupled to a shaft of the detector column;
a motor;
a timing pulley coupled to the shaft of the detector column and coupled to the motor via a belt, wherein the timing pulley comprises a pin, and the motor is configured to rotate the detector column about the longitudinal axis via the timing pulley and the belt;
a pair of optocouplers;
a sweep mechanical stopper configured to rotate between each optocoupler of the pair of optocouplers, wherein the sweep mechanical stopper comprises a protrusion that interacts with each optocoupler to stop rotation of the detector, wherein the sweep mechanical stopper comprises a stopper tooth configured to interact with the pin to enable the timing pulley to rotate the sweep mechanical stopper back and forth between the pair of optocouplers; and
a pair of leaf springs, wherein the pair of leaf springs flanks the pair of optocouplers, and each leaf spring is configured to disengage the protrusion from an optocoupler to enable rotation of the detector column beyond 360 degrees.

13. The radiation detector head assembly of claim 1, wherein the radiation detector head assembly comprises a fan configured to cool the detector column.

14. A detector column for a nuclear medicine multi-head imaging system, comprising:
a detector having a first surface and a second surface opposite the first surface;
a first collimator disposed over the first surface of the detector configured for use during imaging scans involving radiation in a first energy range;
a second collimator disposed over the second surface of the detector configured for use during imaging scans involving radiation in a second energy range different from the first energy range;
radiation shielding encompassing the detector, the first collimator, and the second collimator; and
a module board having digital electronics disposed outside the radiation shielding of the detector column.

15. The detector column of claim 14, wherein the detector column comprises flexible circuits extending from analog electronics coupled to the detector to the module board.

16. The detector column of claim 15, wherein the radiation shielding comprises:
a first radiation shield disposed over the first collimator, wherein the first radiation shield comprises a first recess for receiving the first collimator and a first opening over a third surface of the first collimator, the third surface being opposite the first surface of the detector; and
a second radiation shield disposed over the second collimator, wherein the second radiation shield comprises a second recess for receiving the second collimator and a second opening over a fourth surface of the second collimator, the fourth surface being opposite the second surface of the detector.

17. The detector column of claim 16, wherein the first radiation shield and the second radiation shield form a labyrinth that the flexible circuits extend through to couple to the module board.

18. The detector column of claim 16, wherein the second radiation shield comprises tungsten-filled polymer overmolded on one or more tungsten plates.

19. A radiation detector head assembly, comprising:
a detector column, comprising:
a detector having a first surface and a second surface opposite the first surface;
a first collimator disposed over the first surface of the detector configured for use during imaging scans involving radiation in a first energy range; and
a second collimator disposed over the second surface of the detector configured for use during imaging scans involving radiation in a second energy range different from the first energy range;
wherein the detector column is configured to rotate greater than 360 degrees about its longitudinal axis.

20. The radiation detector head assembly of claim 19, wherein the radiation detector head assembly comprises:
a flexible conductor wrapped around a housing coupled to a shaft of the detector column;
a motor;
a timing pulley coupled to the shaft of the detector column and coupled to the motor via a belt, wherein the timing pulley comprises a pin, and the motor is configured to rotate the detector column about the longitudinal axis via the timing pulley and the belt;
a pair of optocouplers;
a sweep mechanical stopper configured to rotate between each optocoupler of the pair of optocouplers, wherein the sweep mechanical stopper comprises a protrusion that interacts with each optocoupler to stop rotation of the detector, wherein the sweep mechanical stopper comprises a stopper tooth configured to interact with the pin to enable the timing pulley to rotate the sweep mechanical stopper back and forth between the pair of optocouplers; and
a pair of leaf springs, wherein the pair of leaf springs flanks the pair of optocouplers, and each leaf spring is configured to disengage the protrusion from an optocoupler to enable rotation of the detector column beyond 360 degrees.

* * * * *